(12) United States Patent
Gao et al.

(10) Patent No.: US 11,421,241 B2
(45) Date of Patent: Aug. 23, 2022

(54) METHOD FOR CONDUCTING SITE-SPECIFIC MODIFICATION ON ENTIRE PLANT VIA GENE TRANSIENT EXPRESSION

(71) Applicant: Institute of Genetics and Developmental Biology, Chinese Academy of Sciences, Beijing (CN)

(72) Inventors: Caixia Gao, Beijing (CN); Yi Zhang, Taian (CN); Zhongyi Wu, Beijing (CN); Kang Zhang, Tianjin (CN)

(73) Assignee: Institute of Genetics and Developmental Biology, Chinese Academy of Sciences, Beijing (CN)

( * ) Notice: Subject to any disclaimer, the term of this patent is extended or adjusted under 35 U.S.C. 154(b) by 0 days.

(21) Appl. No.: 15/546,481

(22) PCT Filed: Jan. 27, 2016

(86) PCT No.: PCT/CN2016/072352
§ 371 (c)(1),
(2) Date: Jul. 26, 2017

(87) PCT Pub. No.: WO2016/119703
PCT Pub. Date: Aug. 4, 2016

(65) Prior Publication Data
US 2018/0016589 A1 Jan. 18, 2018

(30) Foreign Application Priority Data

Jan. 27, 2015 (CN) .......................... 201510040078.0

(51) Int. Cl.
| C12N 15/82 | (2006.01) |
| C12N 15/89 | (2006.01) |
| C12N 9/22 | (2006.01) |

(52) U.S. Cl.
CPC ........... *C12N 15/8216* (2013.01); *C12N 9/22* (2013.01); *C12N 15/8201* (2013.01); *C12N 15/8213* (2013.01); *C12N 15/8241* (2013.01); *C12N 15/89* (2013.01); *C12N 2310/20* (2017.05)

(58) Field of Classification Search
None
See application file for complete search history.

(56) References Cited

U.S. PATENT DOCUMENTS

| 5,500,360 | A | 3/1996 | Ahlquist et al. |
| 5,736,369 | A | 4/1998 | Bowen et al. |
| 6,187,994 | B1 | 2/2001 | Baszczynski et al. |
| 6,410,329 | B1 | 6/2002 | Hansen et al. |
| 6,603,061 | B1 | 8/2003 | Armstrong et al. |
| 8,399,218 | B2 | 3/2013 | Gupta |
| 8,697,359 | B1 | 4/2014 | Zhang |
| 2003/0135891 | A1 | 7/2003 | Gould et al. |
| 2013/0263324 | A1 | 10/2013 | Lassner et al. |
| 2014/0068797 | A1 | 3/2014 | Doudna et al. |
| 2014/0170753 | A1 | 6/2014 | Zhang |
| 2015/0059010 | A1 | 2/2015 | Cigan |
| 2015/0667922 | | 3/2015 | Yang |
| 2016/0145631 | A1 | 5/2016 | Voytas et al. |
| 2017/0260536 | A1 | 9/2017 | Vainstein et al. |

FOREIGN PATENT DOCUMENTS

| CN | 1541270 A | 10/2004 |
| CN | 102558309 A | 7/2012 |
| CN | 103343120 A | 10/2013 |
| CN | 103382468 A | 11/2013 |
| CN | 103555711 A | 2/2014 |
| CN | 103667338 A | 3/2014 |
| DE | 10 2615 004 187 A1 | 10/2016 |
| EP | 2 274 973 A1 | 1/2011 |
| JP | 2010-539930 A | 12/2010 |

(Continued)

OTHER PUBLICATIONS

Liang et al. Targeted Mutagenesis in *Zea Mays* Using TALENs and the CRISPR/Cas System Journal of Genetics and Genomics 41: 63-68 (Year: 2014).*
Marton et al Nontransgenic Genome Modification in Plant Cells Plant Physiology 154:1079-1087 (Year: 2010).*
Clough and Bent 1998 The Plant Journal 16:735-743, provided by Applicant (Year: 1998).*
International Search Report Issued in PCT/CN2016/072352, dated Apr. 27, 2016, and English Translation thereof, 10 pages.
Jiang, Wenzhi; "Efficient CRISPR/Cas9-Mediated Gene Editing in *Arabidopsis thaliana* and Inheritance of Modified Genes in the T2 and T3 Generations" PLOS ONE, Jun. 11, 2014, vol. 9, No. 6, pp. 1-6.
Liang, Zhen. et al. "Targeted mutagenesis in *Zea mays* using TALENs and the CRISPR/Cas System", Journal of Genetics and Genomics, 2014, vol. 41, pp. 63-68 and Supplemental Table S1 and S2.

(Continued)

*Primary Examiner* — Brent T Page
(74) *Attorney, Agent, or Firm* — Troutman Pepper Hamilton Sanders LLP

(57) ABSTRACT

The present invention discloses a method for site-directed modification of whole plant through gene transient expression. The method as provided for conducting site-directed modification to a target fragment of a target gene in a whole plant comprises the following steps: transiently expressing a sequence-specific nuclease in said plant, wherein a whole plant is used as the subject for transient expression, said sequence-specific nuclease targets and cleaves said target fragment, thereby the site-directed modification is achieved via the self DNA repairing of said plant. In the present invention, tissue culture is omitted by transient expression of the sequence-specific nuclease; mutation is obtained at whole plant level; the method is independent of the genotype and recipient, and thus can be applied to various varieties of various species; T1 mutants can be obtained directly and the mutation can be stable inherited; more importantly, the mutant plant as obtained is free of exogenous genes, and thus have higher bio-safety.

6 Claims, 5 Drawing Sheets
(5 of 5 Drawing Sheet(s) Filed in Color)
Specification includes a Sequence Listing.

(56) References Cited

FOREIGN PATENT DOCUMENTS

| | | |
|---|---|---|
| KR | 1020150006469 | 1/2015 |
| WO | 00/66746 A1 | 11/2000 |
| WO | 2004/009761 A2 | 1/2004 |
| WO | 2009/042164 A1 | 4/2009 |
| WO | 2013/096567 | 6/2013 |
| WO | 2013/142578 A1 | 9/2013 |
| WO | 2013/166315 | 11/2013 |
| WO | 2013/169802 A1 | 11/2013 |
| WO | 2013/176772 A1 | 11/2013 |
| WO | 2014l144155 A1 | 9/2014 |
| WO | 2014194190 A1 | 12/2014 |
| WO | 2015/026885 A1 | 2/2015 |
| WO | 2015/026886 A1 | 2/2015 |
| WO | 2015/066637 A1 | 5/2015 |
| WO | 2015/077290 A2 | 5/2015 |
| WO | 2016/021973 A1 | 2/2016 |
| WO | 2017/092201 A1 | 6/2017 |

OTHER PUBLICATIONS

Shan, Qiwei et al., "Genome editing in rice and wheat using the CRISPR/Cas system", Nature Protocols, 2014, vol. 9, No. 10, pp. 2395-2410.

Voytas, D.F. et al., "Precision Genome Engineering and Agriculture: Opportunities and Regulatory Challenges", PLOS Biology, Jun. 10, 2014, vol. 12, No. 6, e1001877, pp. 1-6.

Wang et al., "Simultaneous editing of three homoeoalleles in hexapioid bread wheat confers heritable resistance to powdery mildew", Nature Biotechnology, 2014, vol. 32, No. 9, pp. 947-952.

Xing et al., "A CRISPR/Cas9 toolkit for multiplex genome editing in plants", BMC Plant Biology, 2014, vol. 14, p. 327, 12 pages.

Armstrong et al., "Development and availability of germplasm with high type II culture formation response", Maize Genet. Coop. News Lett., 1991, vol. 65, pp. 92-93.

Shan et al., "Rapid and efficient gene modification in rice and Brachypodium using TALENs", Molecular Plant, 2013, vol. 6, No. 4, pp. 1365-1368.

Li et al., "Multiplex and homologous recombination-mediated plant genome editing via guide RNA/Cas9". Nature Biotechnology, 2013, vol. 31, No. 8, pp. 688-691.

Luo et al., "A Simple Method for the Transformation of Rice Via the Pollen-Tuba Pathway", Plant Molecular Biology Reporter, 1988, vol. 6, No. 3, pp. 165-174.

Naito et al., "CRISPRdirect: software for designing CRISPR/Cas guide RNA with reduced off-target sites", Bioinfomatics, 2015, vol. 31, No. 7, pp. 1120-1123.

Basic knowledge of the database DIAM biotechnology, (a) Bioindustry Association, "Select temperature," URL:<http://togodb.biosciencedbc.jp/togodb/show/diam_bioterm_list/96>.

Written Opinion issued In PCT/CN2016/072352 dated Apr. 27, 2016 and English Translation thereof.

Russell, "Registration of B70 and B73 parental lines of maize", Crop Sci., 1972, vol. 12, p. 721.

Koornneef et al., "Linkage map of Arabidopsls thaliana", The Journal of Heredity, 1983, vol. 74, pp. 265-272.

Yang et al., "Transgenic soybean with Sow phytate content constructed by Agrobacterium transformation and pollen-tube pathway", Euphytica, 2011, vol. 177, pp. 375-382.

Gasiunas et al., "Cas9-crRNA ribonucleoprotein complex mediates specific DNA cleavage for adaptive immunity in bacteria", Proc. Natl Acad Sci USA, 2012, vol. 109, No. 39, pp. E2579-E2586.

Klein et al.,"Transformation of microbes, plants and animals by particle bombardment", Biotechnology, 1992, vol. 10, No. 3, pp. 286-291.

Shan et al., "Targeted genome modification of crop plants using a CRISPR-Cas System", Nature Biotechnology, vol. 31, No. 8, Aug. 1, 2013, pp. 686-688.

Shan et al., "Supplementary Material for Targeted genome modification of crop plants using a CRISPR-Cas system", Nature Biotechnology, vol. 31, No. 8, Aug. 1, 2013, 19 pages.

Zhang et al., "Transcription Activator-Like Effector Nucleases Enable Efficient Plant Genome Engineering", Plant Physiology, 2013, vol. 161, No. 1, pp. 20-27.

Kumar et al., "The CRISPR-Cas system for plant genome editing: advances and opportunities", Journal of Experimental Botany, 2015, vol. 66, No. 1, pp. 47-57.

Puchta et al., "Synthetic nucleases for genome engineering in plants prospects for a bright future", The Plant Journal, vol. 78, No. 5, 2014, pp. 727-741.

International Search Report and Written Opinion issued PCT/CN2016/071352, dated Apr. 25, 2016, 9 pages.

Ling et al., "Draft genome of the wheat A-genome progenitor Triticum urartu", Nature, 2013, vol. 496, pp. 87-90.

Mao et al., "Overexpression of a NAC-domain protein promotes shoot branching in rice", New Phytologist, 2007, vol. 176, pp. 288-298.

Xu et al., "A PIN1 Family Gene, OsPIN1, involved in Auxin-dependent Adventitious Root Emergence and Tillering in Rice", Plant Cell Physiol., 2005, vol. 46, No. 10, pp. 1674-1681.

Feng et al., "Molecular analysis of lipoxygenase (LOX) genes in common wheat and phylogenetic investigation of LOX proteins from model and crop plants", Journal of Cereal Science, 2010, vol. 52, pp. 387-394.

Lawrenson et al., "Induction of targeted, heritable mutations in barley and Brassica oleracea using RNA-guided Cas9 nuclease", Genome Biology, 2015, vol. 16, 258, 13 pages.

Zhang et al., "Biolistic Genetic Transformation of a Wide Range of Chinese Elite Wheat (Triticum aestivum L.) Varieties", Journal of Genetics and Genomics, 2015, vol. 42, pp. 39-42.

Larsen et al., "ALS3 encodes a phloem-localized ABC transporter-like protein that is required for aluminum tolerance in Arabidopsis", The Plant Journal, 2005, vol. 41, No. 3, pp. 353-363.

Laursen et al., "Production of fertile transgenic maize by electroporation of suspension culture cells", Plant Molecular Biology, 1994, vol. 24, No. 1, pp. 51-61.

Aragao et al., "Particle bombardment-mediated transient expression of a Brazil nut methionine-rich albumin in bean (Phaseolus vulgaris L.)", Plant Molecular Biology, 1992, vol. 20, No. 2, pp. 357-359.

Brooks et al., "Efficient Gene Editing in Tomato in the First Generation Using the Clustered Regularly Interspaced Short Palindromic Repeats/CRISPR-Associated9 System", Plant Physiology, 2014, vol. 166, pp. 1292-1297.

International Search Report and Written Opinion by the International Searching Authority in International Application No. PCT/CN2016/095307 dated Nov. 23, 2016.

Weinthal et al., "Nonhomologous End Joining-Mediated Gene Replacement in Plant Cells", Plant Physiology, 2013, vol. 162, pp. 390-400.

Chen et al., "TALENs: Customizable Molecular DNA Scissors for Genome Engineering of Plants", Journal of Genetics and Genomics, 2013, vol. 40, No. 6, pp. 271-279.

Gilles et al., "Efficient CRISPR-mediated gene targeting and transgene replacement in the beetle Tribolium castaneum", Development, vol. 142, No. 16, 2015, pp. 2832-2839.

Li et al., "Gene replacements and insertions in rice by intron targeting using CRISPR-Cas9", Nature Plants, vol. 2, No. 10, 2016, Article No. 16139, 6 pages.

Zu et al., "TALEN-mediated precise genome modification by homologous recombination in zebrafish", Nature Methods, 2013, vol. 10, No. 4, pp. 329-331.

Kanchiswamy et al., "Non-GMO genetically edited crop plants", Trends in Biotechnology, 2015, vol. 33, No. 9, pp. 489-491.

Xu et al., "Cloning of genomic DAN of rice 5-enolpyruvishikimate 3-phsphate synthase gene and chromosomal localization of the gene", Science in China, 2002, vol. 45, No. 3, pp. 251-259.

Zahir et al., "The Efficient Virus-Mediated Genome Editing in Plants Using the CRISPR/Cas9 System", Molecular Plant, vol. 8, No. 8, 2015, pp. 1288-1291.

(56) References Cited

OTHER PUBLICATIONS

Anonymous: "A Streamlined Method for the Production, Screening, and Application of sgRNAs for CRISPR/Cas9 Gene Editing" Bio Techniques, vol. 57, No. 3, Sep. 2014, p. 157.
Barrangou et al., "CRISPR provides acquired resistance against viruses in prokaryotes", Science, 2007, vol. 315, 1709-1712.
Zetsche et al., "Cpf1 is a single RNA-guided endonuclease of a Class 2 CRISPR-Cas system", Cell, vol. 163, No. 3, 2015, pp. 759-771.
Clough et al., "Floral Dip: a simplified method for Agrobacterium-mediated transformation of *Arabidopsis thaliana*", The Plant Journal, vol. 16, No. 6, 1998, pp. 735-743.
Deltcheva et al., "CRISPR RNA maturation by trans-encoded small RNA and host factor RNase III", Nature, 2011, vol. 471, No. 7340, pp. 602-607.
Gelvin, "Viral-mediated plant transformation gets a boost", Nature Biotechnology, vol. 23, No. 6, 2005, pp. 684-685.
Guilinger et al., "Fusion of catalytically inactive Cas9 to FokI nuclease improves the specificity of genome modification", Nat Biotechnol., 2014, vol. 32, No. 6, pp. 577-582.
Helenius et al., "Gene delivery into intact plants using the Helios Gene Gun", Plant Molecular Biology Reporter, 2000, vol. 18, No. 3, pp. 287a-287l.
International Search Report and Written Opinion issued in International Application No. PCT/EP2016/061237, dated Feb. 20, 2017.
Jansen et al., "Identification of genes that are associated with DNA repeats in pokaryotes", Molecular Microbiology, 2002, vol. 43, No. 6, pp. 1565-1575.
Jinek et al. "A programmable dual-RNA-guided DNA Endonuclease in Adaptive Bacterial Immunity", Science, 2012, vol. 337, pp. 816-821.
Kim et al., "Highly efficient RNA-guided genome editing in human cells via delivery of purified Cas9 ribonucleoproteins", Genome Research, 2014, vol. 24, No. 6, pp. 1012-1019.
Krens et al., "Transformation and regeneration in sugar beet (*Beta vulgaris* L.) induced by 'shooter' mutants of Agrobacterium tumefaciens", Euphytica, 1988, vol. 39, No. 3, pp. 185-194.
Leduc et al., "Gene transfer to inflorescence and flower meristems using ballistic micro-targeting", Sexual Plant Reproduction, 1994, vol. 7, No. 2, pp. 135-143.
Bortesi et al., "The CRISPR/Cas9 system for plant genome editing and beyond", Biotechnology Advances, vol. 33, No. 1, Dec. 20, 2014, pp. 41-52.
Mahn et al., "Transient gene expression in shoot apical meristems of sugarbeet seedlings after particle bombardment", Journal of Experimental Botany, 1995, vol. 46, No. 291, pp. 1625-1628.
Makarova et al., "An updated evolutionary classification of CRISPR-Cas systems", Nature Rev. Microbiol., 2015, vol. 13, No. 11, pp. 722-736.
Makarova at al., "Annotation and Classification of CRISPR-Cas Systems", Methods Mol. Biol., 2015, vol. 1311, pp. 47-75.
Makarova et al., "Unification of Cas protein families and a simple scenario for the origin and evolution of CRISPR-Cas systems", Biology Direct, vol. 6, No. 38, 2011, 27 pages.
Mali et al., "CAS9 transcriptional activators for target specificity screening and paired nickases for cooperative genome engineering", Nat Biotechnol., 2013, vol. 31, No. 9, pp. 833-838.
Martin-Ortigosa et al., "Proteolistics: a biolistic method for intracellular delivery of proteins", Transgenic Research, 2014, vol. 23, pp. 743-756.
Baltes et al., "DNA Replicons for Plant Genome Engineering" The Plant Cell, American Society of Plant Biologist, vol. 26, No. 1, Jan. 17, 2014, pp. 151-163.
Quinn et al., "A Streamlined Method for the Production, Screening, Application of sgRNAs for CRISPR/Cas Gene Editing", Molecular Therapy, vol. 22, Supplement 1, 2014, 2 pages.
Ramakrishna et al., "Gene disruption by cell-penetrating peptide-mediated delivery of Cas9 protein and guide RNA", Genome Research, 2014, vol. 24, No. 6, pp. 1020-1027.

Sapranauskas et al., "The *Streptococcus thermophilus* CRISPR/Cas system provides immunity in *Escherichia coli*", Nucleic Acids Research, 2011, vol. 39, No. 21, pp. 9275-9282.
Maruyama et al., "Inhibition of non-homologous end joining increases the efficiency of CRISPR/Cas9-mediated precise [TM: Inserted] genome editing", Nat Biotechnol, vol. 33, No. 5, May 2015, pp. 538-542.
Jacobs et al., "Targeted genome modifications in soybean with CRISPR/Cas9", BMC Biotechnology, vol. 15, No. 16, 2015, pp. 1-10.
Van der Oost et al., "Unravelling the structural and mechanistic basis of CRISPR-Cas systems", Nat Rev Microbiol., 2014, vol. 12, No. 7, pp. 479-492.
Jiang et al., "Demonstration of CRISPR/Cas9/sgRNA-mediated targeted gene modification in *Arabidopsis*, tobacco, sorghum and rice", Nucleic Acids Research, 2013, vol. 41, No. 20, pp. e188, 12 pages total.
Wiedenheft et al., "Structures of the RNA-guided surveillance complex from a bacterial immune system", Nature, 2011, vol. 477, No. 7365, pp. 486-489.
Yoo et al., "*Arabidopsis mesophyll* protoplasts: a versatile cell system for transient gene expression analysis", Nature Protocols, 2007, vol. 2, No. 7, pp. 1565-1572.
Hyun et al. "Site-directed mutagenesis in *Arabidopsis thaliana* using dividing tissue-targeted RGEN of the CRISPR/Cas System to generate heritable null alleles". Planta, vol. 241, No. 1, Oct. 1, 2014, pp. 271-284.
Zhang et al., "The CRISPR/Cas9 System Produces Specific and Homozygous Targeted Gene Editing in Rice in One Generation," Plant Biotechnology Journal, 2014, vol. 12, No. 6, pp. 797-807.
International Search Report and Written Opinion Issued by the International Searching Authority In International Application No. PCT/EP2016/061338, dated Aug. 5, 2016.
Abhishek et al., "Tissue Culture Independent Agrobacterium tumefaciens Mediated in Planta Transformation Method for Tropical Maize (*Zea mays*. L)", Proceedings of the National Academy of Sciences, India, Section B, Biological Sciences, 2016, vol. 86, No. 2, pp. 375-384.
Bent et al., "*Arabidopsis* in Planta Transformation. Uses, mechanisms, and Prospects for Transformation of Other Species", Plant Physiology, 2000, vol. 124, No. 4, p. 1540-1547.
Chowrira et al., "Transgenic Grain Legumes Obtained by In Planta Electroporation-Mediated Gene Transfer", Molecular Biotechnology, vol. 5, No. 2, 1996, pp. 85-96.
Razzaq et al., "Development of in planta transformation protocol for wheat", African Journal of Biotechnology, vol. 10. No. 5, 2011, pp. 740-750.
Collins et al., "The Effect of Cotyledon Excision on Reproductive Development in Pea (*Pisum sativum* L.)", Annals of Botany, vol. 38, No. 1, 1974, pp. 181-188.
Springer et al., "A Histological Examination of Tissue Culture Initiation From Immature Embryos of Maize",Protoplasma, 1979, vol. 101, pp. 269-281.
Ma et al., "Plant multiplex genome editing vector pYLCRISPR/Cas9P35s-B, complete sequence", GenBank KR 029113, 2015.
European Search Report issued in EP 15202060 dated Aug. 5, 2016.
Hu et al., "Agrobacterium-mediated vacuum infiltration and floral dip transformation of rapid-cycling *Brassica rapa*", BMC Plant Biology, 2019, vol. 19, Article No. 246, 9 pages.
Ghedira et al., "The Efficiency of *Arabidopsis thaliana* Floral Dip Transformation is Determined Not Only by the Agrobacterium Strain Used but Also by the Physiology and the Ecotype of the Dipped Plant", MPMI, vol. 26, No. 7, 2013, pp. 823-832.
Takacs et al., "Ontogeny of the Maize Shoot Apical Meristem", The Plant Cell, vol. 24, Aug. 2012, pp. 3219-3234.
Al-Abed et al. "Split-seed: a new tool for maize researchers", Plante, 2006, vol. 223, pp. 1355-1360.
Feng et al., "Efficient genome editing in plants using a CRISPR/Cas System", Cell Research, 2013, vol. 23, No. 10, pp. 1229-1232.
Woo et al., "DNA-free genome editing in plants with preassembied CRISPR-Cas9 ribonucleoproteins," Nature Biotechnology, vol. 33, No. 11, 2015, pp. 1162-1165.

(56) References Cited

OTHER PUBLICATIONS

Weeks et al., "Rapid production of multiple Independent lines of fertile transgenic wheat (Triticum aestivum)", Plant Physiol., 1993, vol. 102, pp. 1077-1084.
Ishida et al., "Agrobacterium-mediated transformation of maize", Nature Protocols, 2007, vol. 2, No. 7, pp. 1614-1621.
Elhiti et al., "The use of zygotic embryos as explants for in vitro propagation: an overview", Plant Embryo Culture:Methods and Protocols, Thrope et al. Eds., Methods in Molecular Biology, 2011, vol. 710, pp. 229-255.
Carroll, "Genome Engineering with Targetable Nucleases", Annu. Rev. Biochem., 2014, vol. 83, pp. 409-439.
Doshi et al., "Anthocyanin expression in marker free transgenic wheat and triticale embryos", In Vitro Cell Dev. Biol.—Plant, 2007, vol. 43, pp. 429-435.
De Vetten et ai., "A transformation method for obtaining marker-free plants of a cross-pollinating and vegetatively propagated crop", Nature Biotechnology, 2003, vol. 21, No. 4, pp. 439-442.
Pastori et al., "Age-dependent transformation frequency in elite wheat varieties", Journal of Experimental Botany, 2001, vol. 52, No. 357, pp. 857-863.

\* cited by examiner

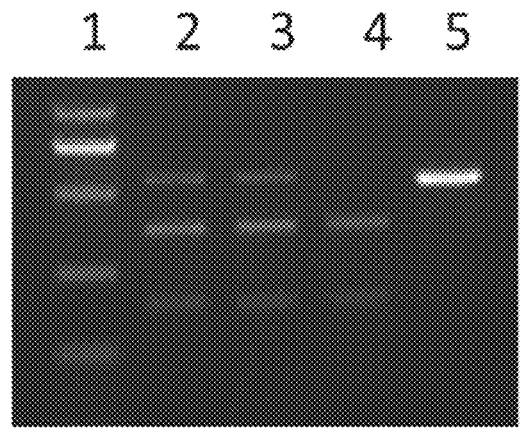

Fig 1A

```
CCATGCTCCAGGTCGTCTCCGAGCTCGACCACGCCGCCGACCAGGACAGCACTTT-3'      WT   (SEQ ID NO: 28)
CCATGCTCCAGGTCGTCTCCGAGC.CGACCACGCCGCCGACCAGGACAGCACTTT        -1bp  (SEQ ID NO: 29)
CCATGCTCCAGGTCGTCTCCGAGCaTCGACCACGCCGCCGACCAGGACAGCACTTT       +1bp  (SEQ ID NO: 30)
CCATGCTCCAGGTCGTCTCCG........CACGCCGCCGACCAGGACAGCACTTT        -8bp  (SEQ ID NO: 31)
```

Fig. 1B

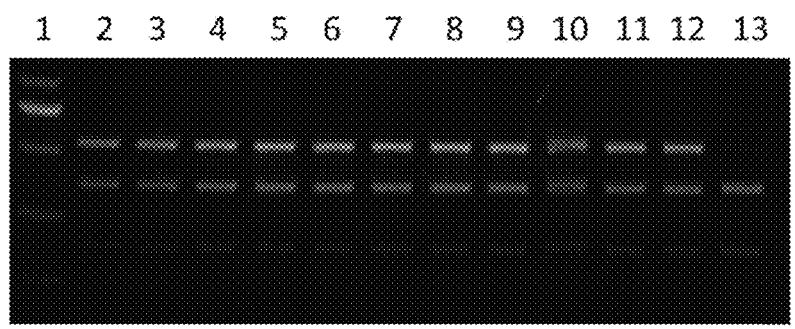

Fig. 2A

```
CCATGCTCCAGGTCGTCTCCGAGCTCGACCACGCCGCCGACCAGGACAGCACTTT-3'      WT   (SEQ ID NO: 28)
CCATGCTCCAGGTCGTCTCCGAGC..........CGCCGACCAGGACAGCACTTT       -10bp  (SEQ ID NO: 32)
CCATGCTCCAGGTCGTCTCCGAG.....CCACGCCGCCGACCAGGACAGCACTTT        -5bp  (SEQ ID NO: 33)
CCATGCTCCAGGTCGTCTCCGA......CCACGCCGCCGACCAGGACAGCACTTT        -6bp  (SEQ ID NO: 34)
```

Fig. 2B

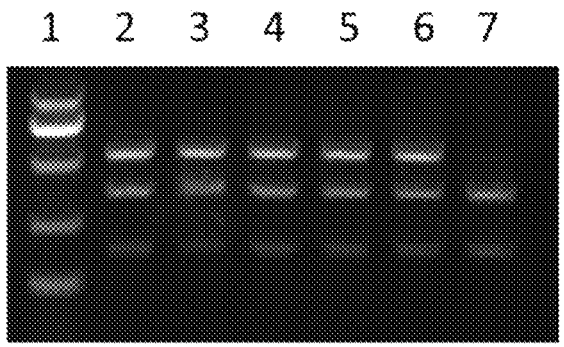

Fig. 3A

```
CCATGCTCCAGGTCGTCTCCGAGCTCGACCACGCCGCCGACCAGGACAGCACTTT-3'   WT   (SEQ ID NO: 28)
CCATGCTCCAGGTCGTCTCCGAG..CGACCACGCCGCCGACCAGGACAGCACTTT     -2bp (SEQ ID NO: 35)
CCATGCTCCAGGTCGTCTCCGAGCtTCGACCACGCCGCCGACCAGGACAGCACTTT    +1bp (SEQ ID NO: 36)
CCATGCTCCAGGTCGTCTCCGA.......CACGCCGCCGACCAGGACAGCACTTT     -7bp (SEQ ID NO: 37)
```

Fig. 3B

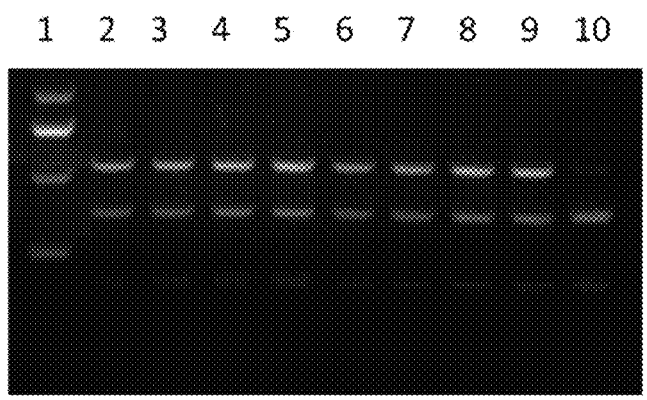

Fig. 4A

```
CCATGCTCCAGGTCGTCTCCGAGCTCGACCACGCCGCCGACCAGGACAGCACTTT-3'   WT    (SEQ ID NO: 28)
CCATGCTCCAGGTCGTCTCCGAG...........CGCCGACCAGGACAGCACTTT      -11bp (SEQ ID NO: 38)
CCATGCTCCAGGTCGTCTCCGAGC.........CCGCCGACCAGGACAGCACTTT      -9bp  (SEQ ID NO: 39)
CCATGCTCCAGGTCGTCTCCGAG..CGACCACGCCGCCGACCAGGACAGCACTTT      -2bp  (SEQ ID NO: 40)
```

Fig. 4B

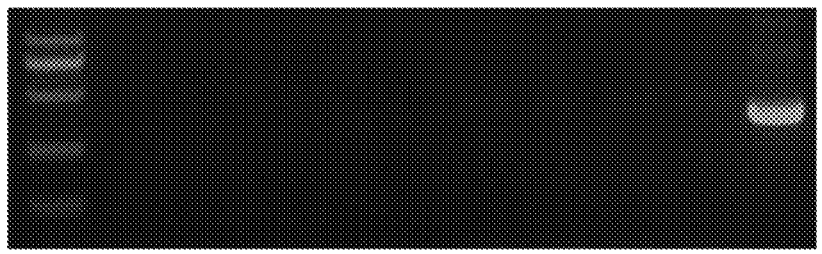
Fig. 5A
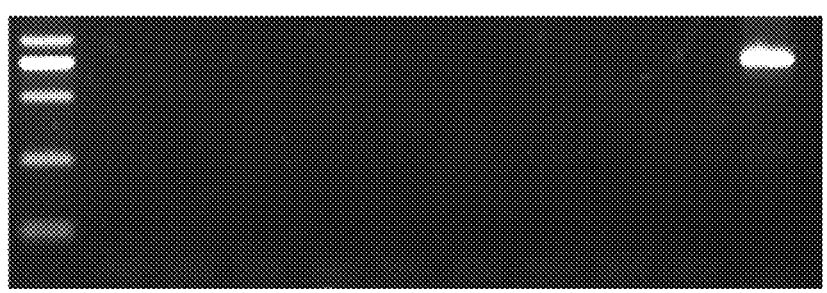
Fig. 5B
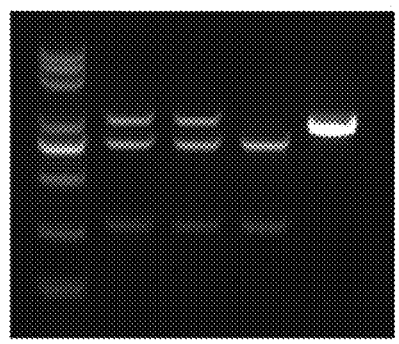
Fig. 6A
```
CTATCATTTCCAATCTCCGTCAAACGAATCCACTCTCCCGACGTATACCGCCGATTTCACGAATCCGCT-3'    WT    (SEQ ID NO: 41)
CTATCATTTC------------------------------------------------ACGAATCCGCT      -48bp (SEQ ID NO: 42)
CTATCATTTCCAATCTCCGTCAAACGAATCCACTCTCCCGACGTATACCGCCGATTTCACGAATCCGCT      +1bp  (SEQ ID NO: 43)
```
Fig. 6B

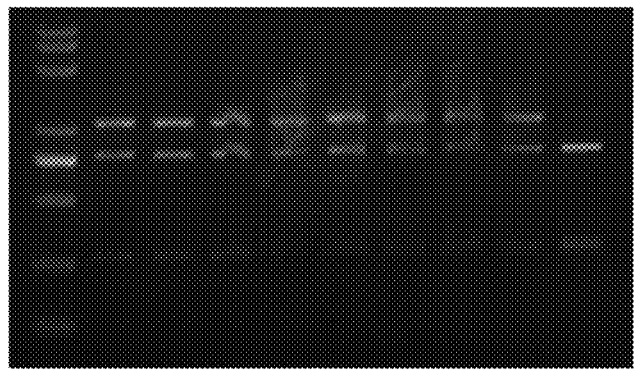

Fig. 7A

```
CTATCATTTCCAATCTCCCGTCAAACGAATCCACTCTCCCGACG-ATATCCGCCGATTTCACGAATCCGCT    WT      (SEQ ID NO: 41)
CTATCATTTC------------------------------------------------ACGAATCCGCT    -49bp   (SEQ ID NO: 42)
CTATCATTTCCAATCTCCCGTCAAACGAATCCACTCTCCCGACG ATATCCGCCGATTTCACGAATCCGCT    +1bp    (SEQ ID NO: 43)
CTATCATTTCCAATCTCCCGTCAAACGAATCCACTCTCCCGAC----ATATCCGCCGATTTCACGAATCCGCT  -1bp    (SEQ ID NO: 44)
CTATCATTTCCAATCTCCCGTCAAACGAATCCACTCTCCCGA--------------CGACGATTTCACGAATCCGCT  -7bp  (SEQ ID NO: 45)
CTATCATTTCCAATCTCCCGTCAAACGAATCCACTCTCCGA----------------CGATTTCACGAATCCGCT  -10bp   (SEQ ID NO: 46)
CTATCATTTCCAAT--------------------------------ATCCGCCGATTTCACGAATCCGCT    -32bp   (SEQ ID NO: 47)
```

Fig. 7B

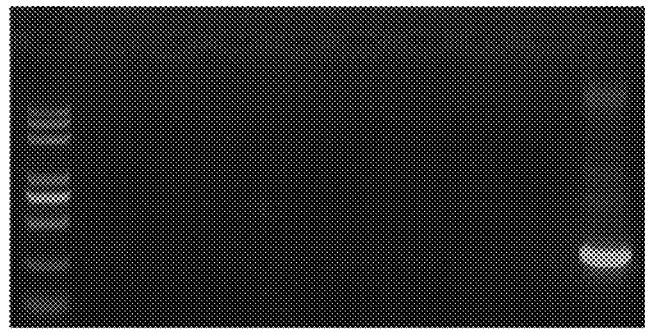

Fig. 8A

METHOD FOR CONDUCTING SITE-SPECIFIC MODIFICATION ON ENTIRE PLANT VIA GENE TRANSIENT EXPRESSION

CROSS-REFERENCE TO RELATED APPLICATIONS

This application is a U.S. National Phase of International Patent Application No. PCT/CN2016/072352, filed on Jan. 27, 2016, which published as WO2016/119703 A1 on Aug. 4, 2016, and claims priority to Chinese Patent Application No. 201510040078.0, filed on Jan. 27, 2015, all of which are herein incorporated by reference in their entirety.

SEQUENCE LISTING

The instant application contains a Sequence Listing which has been submitted in ASCII format via EFS-Web and is hereby incorporated by reference in its entirety. Said ASCII copy, created on Feb. 4, 2019, is named KWS0242PCT_US_SQL_ST25.txt, and is 24,486 bytes in size.

TECHNICAL FIELD

The present invention belongs to the field of plant genetic engineering, and is related to method for site-directed modification of whole plant through gene transient expression.

TECHNICAL BACKGROUND

Transgenesis refers to a process of transferring exogenous gene(s) into a specific organism via molecular biology means so that the biological characteristics or functions of the organism are partially changed. In 1983, the first transgenic plant in the world, transgenic antiviral tobacco was bred in USA. In 1986, transgenic antiviral cotton was developed in USA and subjected to field trials. In 1987, insect-resistant gene and herbicide-resistant gene were transferred into crops. In 1992, transgenic tobacco was grown in China. In 1995, Canada started commercializing transgenic herbicide-resistant *Brassica*. In 1996, transgenic insect-resistant cotton and herbicide-resistant soy bean were grown in large scale in USA. Currently, there are more than 120 transgenic plants in the world, in which 51 transgenic crops including soy bean, cotton and maize, have been commercialized.

Currently, more and more concerns about transgenic products are raised, especially for the safety of transgenic foods. The regulation to transgenic organisms is very strict in most countries. Lots of money and time will be cost to control a transgenic technique or product. According to the investigation of International Crop Life, it would require about 5.5 years and 35 million US dollars for commercialization of a transgenic event. In addition, those transgenic crops already commercialized are not well accepted by the market, for example, the first transgenic tomato allowed for sale eventually exits the market due to poor sales. Therefore, it is very important to develop transgene-free methods for crop improvement.

Currently, methods for genetically improvement of a crop or gene modification have many defects. For example, traditional cross breeding needs to be conducted for several generations, and thus is time-consuming and requires excessive work. It may also be limited by interspecies reproductive isolation and affected by undesirable gene linkage. Physical or chemical mutagenesis methods, such as radiation mutagenesis, EMS mutagenesis etc., can randomly introduce a large number of mutated sites in the genome, but the identifications of the mutated sites would be very difficult.

Genomic site-directed modification tools, which are novel techniques arisen in recent years, mainly include three categories of sequence specific nucleases (SSN): Zinc finger nucleases (ZFN), Transcription activator-like effector nucleases (TALEN), and Clustered regularly interspaced short palindromic repeats/CRISPR associated systems (CRISPR/Cas9). Their common feature is that they can act as an endonuclease to cleave specific DNA sequences, producing DNA double-strand break (DSB). The DSB can activate intrinsic repair mechanism of the cell, Non-homologous end joining (NHEJ) and Homologous recombination (HR), so as to repair the DNA damages. Site-directed modification to a specific DNA sequence can be achieved during the DNA repair process.

Using gene transfer techniques to deliver the above tools into crops can overcome the defects of traditional breeding, such as low efficiency, time-consuming, and poor specificity. However, this process involves transgenes and thus site-directed modified mutant free of transgene has to be obtained through segregation in the progeny population. Since exogenous genes have been integrated into the plant genome (although finally removed by segregation), safety concerns still exist. Therefore, there is still a need of a method for site-directed modification of crops which avoids transgenes.

Conventional gene transfer means, such as particle bombardment transformation, *Agrobacterium*-mediated transformation or protoplast-based transformation, requires the process of tissue culture. Plant tissue culture means that desired tissues, cells or protoplasts are isolated from the plant, and cultured under artificial conditions to regenerate a whole plant. Tissue culture tends to produce somatic mutations, and is limited by plant genotype and specific recipient. It requires a long time to obtain the regenerated plant and costs a lot of resources. In situ transformation means transformation of a living plant (not ex vivo), without the need of tissue or cell culture. In situ transformation generally uses a whole plant as the subject for transformation and includes, such as, pollen tube approach, inflorescence-dipping, shoot apex regeneration, ovary injection, leaf disc approach and the like. In situ transformation avoids tissue culture and thus is easy to perform and requires no specific equipments. This method is independent of the genotype and recipient and thus can be applied to different varieties of different species. In addition, transgenic offspring can be obtained directly. Therefore, site-directed modification to a plant genome can be achieved by transient expression system via in situ transformation, which has benefit for the application of gene editing techniques in plants.

SUMMARY OF THE INVENTION

The object of the invention is to provide a method for site-directed modification of a whole plant through gene transient expression.

The present invention provides a method for conducting site-directed modification to a target fragment of a target gene in a plant, which may comprises the following steps: transiently expressing a sequence-specific nuclease in the plant of interest, wherein the whole plant is used as the subject for transient expression, said sequence-specific nuclease targets and cleaves said target fragment, thereby the site-directed modification is achieved via the self DNA repairing of said plant. This method does not involve a tissue culture process.

In one embodiment of said method, the approach for transiently expressing said site-directed nuclease in said plant comprises the following steps:

a) delivering the sequence-specific nuclease or a genetic material for expressing the sequence-specific nuclease into said plant, and b) growing the plant obtained in step a) in the absence of selection pressure, thereby the sequence-specific nuclease or the genetic material not integrated into the plant chromosome is degraded.

In one embodiment of the method of the invention, said genetic material is a recombinant vector (such as a DNA plasmid) or a DNA linear fragment or an in vitro transcribed RNA.

In the absence of selection pressure, the defending system of the plant will inhibit the entry of an exogenous gene and degrade the exogenous gene that has already been delivered into the plant. Therefore, when growing the whole plant which has undergone transient expression, the exogenous gene (including any fragment of the genetic material for expressing the nuclease specific to the target fragment) will not be integrated into the genome of the plant, and the plant finally obtained is a transgene-free plant with site-directed modification.

In one embodiment of the method of the invention, the sequence-specific nuclease or the genetic material is delivered via any part of plant which can be used for the delivery of the sequence-specific nuclease or the genetic material, such as a pollen tube, inflorescence, shoot apex, ovary, or leaf etc.

In one embodiment where said part of plant is a pollen tube, the delivery is performed by injecting a solution containing recombinant vector (such as a DNA plasmid) or DNA linear fragment or in vitro transcribed RNA or a solution containing said sequence-specific nuclease into the stigma after pollination, thereby the exogenous genetic material or the sequence-specific nuclease is delivered into the fertilized ovum via the pollen tube which is formed during flowering and fertilization (namely, the pollen tube approach).

In one embodiment where said part of plant is an inflorescence, the delivery is performed by dipping the inflorescence with a solution of *Agrobacterium tumefaciens* carrying recombinant vector (such as a DNA plasmid) or DNA linear fragment (namely, inflorescence-dipping or floral-dip approach).

In one embodiment where said part of plant is a shoot apex, the delivery is performed by dipping the shoot apex with a solution of *Agrobacterium tumefaciens* carrying recombinant vector (such as a DNA plasmid) or DNA linear fragment (namely, shoot apex regeneration approach).

In one embodiment where said part of plant is an ovary, the delivery is performed by injecting a solution containing recombinant vector (such as a DNA plasmid) or DNA linear fragment or in vitro transcribed RNA or a solution containing said sequence-specific nuclease into the ovary after pollination (namely, ovary injection approach).

In one embodiment where said part of plant is an ovary, the delivery is performed by injecting a solution of *Agrobacterium tumefaciens* carrying recombinant vector (such as a DNA plasmid) or DNA linear fragment into the ovary after pollination (namely, *Agrobacterium* ovary injection approach).

In one embodiment where said part of plant is a leaf, the delivery is performed by injecting a solution of *Agrobacterium tumefaciens* carrying recombinant vector (such as a DNA plasmid) or DNA linear fragment into the leaf (namely, leaf disc approach).

In said method, the sequence-specific nuclease which is specific to the target fragment can be any nuclease that can achieve genome editing, such as Zinc finger nuclease (ZFN), and Transcription activator-like effector nuclease (TALENs), and CRISPR/Cas9 nuclease etc.

In one embodiment of the invention, the "sequence-specific nuclease" specifically refers to CRISPR/Cas9 nucleases. In some embodiments, the genetic material for expressing the CRISPR/Cas9 nucleases specific to a target fragment is specifically composed of a recombinant vector or DNA fragment for transcribing a guide RNA (or two recombinant vectors or DNA fragments for transcribing crRNA and tracrRNA respectively) and for expressing Cas9 protein; or is specifically composed of a recombinant vector or DNA fragment for transcribing a guide RNA (or two recombinant vectors or DNA fragments for transcribing crRNA and tracrRNA respectively) and a recombinant vector or DNA fragment or RNA for expressing Cas9 protein; or is specifically composed of a guide RNA (or a crRNA and a tracrRNA) and a recombinant vector or DNA fragment or RNA for expressing Cas9 protein. Said guide RNA is an RNA with a palindromic structure which is formed by partial base-pairing between crRNA and tracrRNA; said crRNA contains an RNA fragment capable of complementarily binding to the target fragment.

Furthermore, in the recombinant vector or DNA fragment for transcribing the guide RNA, the promoter for initiating the transcription of the coding nucleotide sequence of said guide RNA is a U6 promoter or a U3 promoter.

More specifically, the recombinant vector for transcribing guide RNA and expressing Cas9 protein is a recombinant plasmid that is obtained by inserting the encoding sequence of the "RNA fragment capable of complementarily binding to the target fragment" in a forward direction between two BsaI restriction sites of plasmid pHSN40 or pHSN401.

The recombinant vector for transcribing the guide RNA is a recombinant plasmid that is obtained by inserting the encoding sequence of the "RNA fragment capable of complementarily binding to the target fragment" in a forward direction between two BbsI restriction sites of plasmid pZmU3-gRNA; the recombinant vector for expressing the Cas9 nuclease is specifically the vector pJIT163-Ubi-Cas9

In another embodiment of the invention, the "sequence-specific nuclease" is TALENs nucleases. The genetic material for expressing the sequence-specific nuclease specific to the target site may be a recombinant vector (DNA plasmid) or DNA fragment or RNA that expresses paired TALEN proteins, wherein the TALEN protein is composed of a DNA binding domain capable of recognizing and binding to the target fragment, and a Fok I domain.

In the case that the sequence-specific nuclease is Zinc finger nucleases (ZFN), the genetic material for expressing the sequence-specific nuclease which is specific to the target site may be a recombinant vector (DNA plasmid) or DNA fragment or RNA that expresses paired ZFN proteins, wherein the ZFN protein is composed of a DNA binding domain capable of recognizing and binding to the target fragment, and a Fok I domain.

In said method, the site-directed modification is specifically insertion, deletion, and/or replacement in the target fragment in the plant genome. In some embodiments, the target fragment is within the encoding region of a target gene. In some embodiments, the target fragment is within the transcription regulation region of a target gene, such as a promoter. In some embodiments, the target gene could be a structural gene or a non-structural gene. In some embodiments, said modification results in loss of function of the target gene. In some embodiments, said modification results in gain (or change) of function of the target gene.

In some embodiments, the plant can be of any genotype. The plant can be monocotyledon or dicotyledon, such as maize (*Zea mays*), wheat, soy bean, cotton, tobacco, *Arabidopsis*, rye, *Rosa roxbunghii*, *Eriobotrya japonica*, *Carica papaya*, *Rosa canina*, *Dendrobium nobile* Lindl., *Brassica oleracea*, *Fagopyrum tataricum*, or *Hevea brasiliensis*.

When the plant is maize, wheat, soy bean, cotton, tobacco and the like, the sequence-specific nuclease or the genetic material may be delivered by the pollen tube approach. When the plant is *Arabidopsis*, wheat, rye and the like, the sequence-specific nuclease or the genetic material may be delivered by the inflorescence-dipping approach. When the plant is maize, *Rosa roxbunghii*, *Eriobotrya japonica*, *Carica papaya*, *Rosa canina* and the like, the genetic material may be delivered by the shoot apex regeneration approach. When the plant is wheat, soy bean, cotton, *Dendrobium nobile* Lindl. and the like, the sequence-specific nuclease or the genetic material may be delivered by the ovary injection approach. When the plant is tobacco, *Brassica oleracea*, *Fagopyrum tataricum*, *Hevea brasiliensis* and the like, the genetic material may be delivered by the leaf disc approach.

In one embodiment (Example 1) of the invention, the plant is maize (in particular, maize hybrid HiII and inbred line B73, Zheng58 etc.); the nuclease is CRISPR/Cas9; the target gene is maize endogenous gene ZmIPK; the target fragment is 5'-AGCTCGACCACGCCGCCGAC-3' (SEQ ID NO: 6); the recombinant vector for transcribing the guide RNA is a recombinant plasmid that is obtained by inserting the DNA fragment as shown in 5'-AGCAGTCGGCGGCGTGGTCGAGCT-3' (SEQ ID NO: 7) in a forward direction between two BbsI restriction sites of plasmid pZmU3-gRNA; the recombinant vector for expressing the Cas9 nuclease is specifically the vector pJIT163-Ubi-Cas9; the recombinant vector for transcribing guide RNA and expressing Cas9 protein is a recombinant plasmid that is obtained by inserting the DNA fragment as shown in 5'-GGCGGTCGGCGGCGTGGTCGAGCT-3' (SEQ ID NO: 8) in a forward direction between two BsaI restriction sites of plasmid pBUE411.

In another embodiment (Example 2) of the invention, the plant is *Arabidopsis*; the nuclease is CRISPR/Cas9; the target gene is *Arabidopsis* endogenous gene AtPTPA; the target fragment is 5'-ACGATATCCGCCGATTTCAC-3' (SEQ ID NO: 9); the recombinant vector for transcribing guide RNA and expressing Cas9 protein is a recombinant plasmid that is obtained by inserting the DNA fragment as shown in 5'-ATTGGTGAAATCGGCGGATATCGT-3' (SEQ ID NO: 10) in a forward direction between two BsaI restriction sites of plasmid pHSN401.

A transgene-free mutant plant and/or an offspring thereof obtained by using the method of the invention to conduct site-directed modification to a target fragment of a target gene in a plant of interest so as to allow the target gene to lose its functions, also fall within the scope of the invention.

The present invention also provides a method for making a transgene-free mutant plant, comprising the following steps: performing site-directed modification to a target fragment of a target gene in a plant of interest using the method of the invention, so as to obtain a plant in which the functions of the target gene are lost and the genome is free of integrated exogenous gene.

As used herein, a transgenic plant refers to a plant with an exogenous gene integrated into the genome thereof. A transgene-free plant refers to a plant without an exogenous gene integrated into the genome thereof.

The present invention combines the genome editing technique and the transient expression system in which a whole plant is used as the subject for expression. That is to say, in the present invention, sequence-specific nuclease is introduced into the cells or tissues in a whole plant via pollen tube approach, inflorescence-dipping, shoot apex regeneration, ovary injection, leaf disc approach and the like; then modification of the plant genome is achieved by the transient expression of the sequence-specific nuclease. Mutant offspring with high safety can be obtained directly. For example, in the pollen tube approach, a solution containing the sequence-specific nuclease or DNA/RNA for expressing the sequence-specific nuclease is delivered into the fertilized egg cells or germ cells (sperm or ovum) through the pollen tube formed during flowering or fertilization of the plant. These cells are protoplast-like (no cell wall formation) and undertake active DNA replication and recombination, and thus will be efficiently edited by the sequence-specific nuclease. The modified fertilized egg cells or germ cells may develop into intact mutant plants. The introduced sequence-specific nuclease or RNA encoding the sequence-specific nuclease will be degraded by the plant cells. DNA encoding the sequence-specific nuclease will also be degraded by the plant cells as the method is performed completely in the absence of selection pressure. Therefore, no exogenous gene will be integrated in the genome and the mutants as obtained will have higher bio-safety.

The advantages of the present invention include: tissue culture is omitted; mutation is obtained at whole plant level; the method is independent of the genotype and recipient, and thus can be applied to various varieties of various species; T1 mutants can be directly obtained and the mutation can be stably inherited; more importantly, the mutant plant as obtained is free of exogenous genes, and thus has higher bio-safety.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-1B show the site-directed mutagenesis of maize endogenous gene ZmIPK by transient expression of gRNA: Cas9 system in protoplast. 1A) is a gel electrophoretogram. Lane 1 is a marker, from bottom to top: 250, 500, 750, 1000 bp respectively; lane 2 and lane 3 are SacI restriction digestion results for PCR products of protoplast DNA, wherein the protoplast were transformed with the gRNA: Cas9 system; lane 4 is SacI digestion result for PCR product of wild-type protoplast DNA; lane 5 is the PCR product of wild-type protoplast. 1B) is the sequencing results of some mutants.

FIGS. 2A-2B show the site-directed mutagenesis of maize endogenous gene ZmIPK by transient expression of gRNA: Cas9 system in maize variety HiII via the pollen tube approach, as well as the sequencing results. 2A) is a gel electrophoretogram. Lane 1 is a marker, from bottom to top: 100, 250, 500, 750, 1000 bp respectively; lanes 2-12 are SacI restriction digestion results for PCR products of the mutants;

Figure 8B:

lane 13 is SacI digestion result for PCR product of wild-type control. 2B) is the sequencing results of some mutants.

FIGS. 3A-3B show the site-directed mutagenesis of maize endogenous gene ZmIPK by transient expression of gRNA: Cas9 system in maize variety B73 via the pollen tube approach, as well as the sequencing results. 3A) is a gel electrophoretogram. Lane 1 is a marker, from bottom to top: 100, 250, 500, 750, 1000 bp respectively; lanes 2-6 are SacI restriction digestion results for PCR products of the mutants; lane 7 is SacI digestion result for PCR product of wild-type control. 3B) is the sequencing results of some mutants.

FIGS. 4A-4B show the site-directed mutagenesis of maize endogenous gene ZmIPK by transient expression of gRNA: Cas9 system in maize variety Zheng58 via the pollen tube approach, as well as the sequencing results. 4A) is a gel electrophoretogram. Lane 1 is a marker, from bottom to top: 100, 250, 500, 750, 1000 bp respectively; lanes 2-9 are SacI restriction digestion results for PCR products of the mutants; lane 10 is SacI digestion result for PCR product of wild-type control. 4B) is the sequencing results of some mutants.

FIGS. 5A-5B depict a gel electrophoretogram showing the amplification of ZmIPK gene mutants from different maize varieties via the pollen tube approach, using 2 primer sets on the pZmU3-gRNA-C1 and pJIT163-Ubi-Cas9 vectors. 5A) is the amplification result using the primer pair ZmU3-F/C1R; 5B) is the amplification result using the primer pair Cas9-1F/Cas9-1R. Lane 1 is a marker, from bottom to top: 100, 250, 500, 750, 1000 respectively; lanes 2-10 are mutants as tested; lane 11 is the positive control (plasmid pZmU3-gRNA-C1 or pJIT163-Ubi-Cas9).

FIGS. 6A-6B shows the site-directed mutagenesis of *Arabidopsis* endogenous gene AtPTPA by transient expression of gRNA:Cas9 system in protoplast. 6A) is a gel electrophoretogram. Lane 1 is a marker, from bottom to top: 100, 250, 500, 750, 1000 bp, 2000, 3000, 5000 bp, respectively; lane 2 and lane 3 are EcoRV restriction digestion results for PCR products of protoplast DNA, wherein the protoplast were transformed with the gRNA:Cas9 system; lane 4 is EcoRV digestion result for PCR product of wild-type protoplast DNA; lane 5 is the PCR product of wild-type protoplast. 6B) is the sequencing results of the uncut bands.

FIGS. 7A-7B shows the site-directed mutagenesis of *Arabidopsis* endogenous gene AtPTPA by transient expression of gRNA:Cas9 system via the inflorescence-dipping approach. 7A) is a gel electrophoretogram. Lane 1 is a marker, from bottom to top: 100, 250, 500, 750, 1000 bp, 2000, 3000, 5000 bp, respectively; lanes 2-9 are EcoRV restriction digestion results for PCR products of the mutants; lane 10 is EcoRV digestion result for PCR product of wild-type control. 7B) is the sequencing results of some mutants.

FIGS. 8A-8B is a gel electrophoretogram showing the amplification of AtPTPA gene mutants using primers on the pHSN401-C2 vector. 8A) is the amplification result using the primer pair pHSN401-1F/C2R; 8B) is the amplification result using the primer pair CAS9-2F/CAS9-2R. Lane 1 is a marker, from bottom to top: 100, 250, 500, 750, 1000 bp, 2000, 3000, 5000 bp respectively; lanes 2-9 are mutants as tested; lane 10 is the positive control (plasmid pHSN401).

Figure 9:
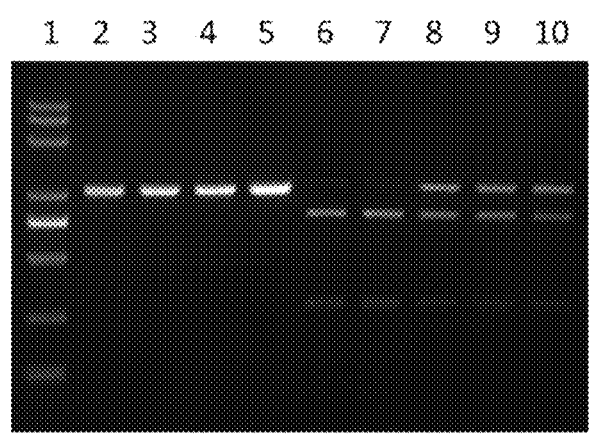

FIG. 9 shows the mutation in the progeny of the AtPTPA gene mutants. Lane 1 is a marker, from bottom to top: 100, 250, 500, 750, 1000, 2000, 3000, 5000 bp respectively; lanes 2, 3, 4, 5 are progeny of homozygous mutants; lanes 6-7 are wild type progeny obtained by segregation; lanes 8, 9, 10 are progeny of heterozygous mutants.

DETAILED EMBODIMENTS

The experimental methods used in the following Examples are all conventional methods, unless otherwise indicated.

The materials, reagents used in the following Examples are all commercially available, unless otherwise indicated.

Expression vector pZmU3-gRNA was disclosed in "Liang, Z. et al. Targeted mutagenesis in *Zea mays* using TALENs and the CRISPR/Cas System. Journal of Genetics and Genomics. 41:63-68, (2014)".

Expression vectors pJIT163-Ubi-Cas9 was disclosed in "Wang, Y. et al. Simultaneous editing of three homoeoalleles in hexaploid bread wheat confers heritable resistance to powdery mildew. Nature Biotechnology. 32, 947-951 (2014)".

Expression vectors pHSN401 and pBUE411 were disclosed in "Xing, H. et al. A CRISPR/Cas9 toolkit for multiplex genome editing in plants. BMC Plant Biology. 14:327, (2014)".

Maize variety HiII was disclosed in "Armstrong, C. L., Green, C. E.& Phillips, R. L. Development and availability of germplasm with high type II culture formation response. Maize Genet. Coop. News Lett. 65, 92-93 (1991)".

Maize variety B73 was disclosed in "Russell, W. A. Registration of B70 and B73 parental lines of maize. Crop Sci. 12, 721 (1972)".

Maize variety Zheng58 was disclosed in "Zhang Falin, Breeding and application of a Maize inbred line Zheng58. Crop Journal, 2001(4):31-31".

*Arabidopsis thaliana* ecotype Columbia was disclosed in "Koorneef, M. et al. Linkage map of *Arabidopsis thaliana*. Journal of Heredity. 74, 265-272 (1983)".

MS medium: 4.43 g/L MS salts (Sigma, M5524), 30 g/L sucrose, 3 g/L phytogel, pH 5.7, autoclaved at 121° C. for 20 min.

LB medium: 10 g/L Tryptone, 5 g/L Yeast Extract, 10 g/L NaCl, pH7.0 (for solid LB medium, 15 g agar was added per liter liquid medium), autoclaved at 121° C. for 20 min.

Solutions used in the preparation and transformation of protoplast are shown in Tables 1-6.

TABLE 1

| 50 ml enzymolysis solution for *Arabidopsis* | | |
|---|---|---|
| | The amount added | Final Concentration |
| Cellulase R10 | 0.75 g | 1.5% |
| Macerozyme R10 | 0.15 g | 0.3% |
| mannitol | 3.6434 g | 0.4M |
| 2-(N-Morpholino)ethanesulfonic acid | 0.2132 g | 20 mM |
| KCl | 0.07456 g | 20 mM |
| made up to 50 ml with double distilled water, pH adjusted to 5.7 with KOH; incubated in 55° C. water bath for 10 min, and cooled at room temperature before adding | | |
| $CaCl_2$ | 0.0735 g | 10 mM |
| BSA | 0.05 g | 0.1% |
| filtered with a 0.45 μm filter | | |

TABLE 2

50 ml enzymolysis solution for Maize

| | The amount added | Final Concentration |
|---|---|---|
| Cellulase R10 | 0.75 g | 1.5% |
| Macerozyme R10 | 0.15 g | 0.3% |
| mannitol | 5.4651 g | 0.6M |
| 2-(N-Morpholino)ethanesulfonic acid | 0.1066 g | 10 mM |
| made up to 50 ml with double distilled water, pH adjusted to 5.7 with KOH; incubated in 55° C. water bath for 10 min, and cooled at room temperature before adding | | |
| CaCl$_2$ | 0.00735 g | 1 mM |
| BSA | 0.05 g | 0.1% | filtered with a 0.45 μm filter

TABLE 3

500 ml W5

| | The amount added | Final Concentration |
|---|---|---|
| NaCl | 4.5 g | 154 mM |
| CaCl$_2$ | 9.189 g | 125 mM |
| KCl | 0.1864 g | 5 mM |
| 2-(N-Morpholino)ethanesulfonic acid | 0.4264 g | 4 mM | made up to 500 ml with double distilled water, pH adjusted to 5.7 with NaOH

TABLE 4

250 ml WI solution

| | The amount added | Final Concentration |
|---|---|---|
| mannitol | 27.324 g | 0.6 M |
| KCl | 0.07456 g | 4 mM |
| 2-(N-Morpholino)ethanesulfonic acid (200 mM) | 0.2135 g | 4 mM | made up to 250 ml with double distilled water, pH adjusted to 5.7 with KOH

TABLE 5

10 ml MMG solution

| | The amount added | Final Concentration |
|---|---|---|
| mannitol (0.8M) | 5 ml | 0.4M |
| MgCl$_2$ (1M) | 0.15 ml | 15 mM |
| 2-(N-Morpholino)ethanesulfonic acid (200 mM) | 0.2 ml | 4 mM |
| double distilled water | Made up to 10 ml | |

TABLE 6

4 ml PEG solution

| | The amount added | Final Concentration |
|---|---|---|
| PEG4000 | 1.6 g | 40% |
| mannitol (0.8M) | 1 ml | 0.2M |
| CaCl$_2$ (1M) | 0.4 ml | 0.1M |
| double distilled water | Made up to 4 ml | |

% in above Tables 1-6 indicates weight-volume percentage, g/100 ml.

Transformation of *Agrobacterium tumefaciens*:

1) Competent cells (stored at −80° C.) were thawed on ice, then 2 μg plasmid DNA was added and mixed; the mixture was placed on ice for 30 min;

2) the EP tube was submerged in liquid nitrogen for 1 min, and transferred quickly to a 37° C. water bath for thawing (2 min);

3) then 1 ml LB liquid medium was added and incubated at 28° C. for 4-5 h with shaking at a low speed (150 rpm);

4) bacteria cells were harvested by centrifuging at 10000 rpm for 30 s, the supernatant was discarded, and 100 μl resuspended bacteria cells were plated on the selection plates containing corresponding antibiotics.

5) plates were incubated upside down at 28° C. until white colonies (transformants) emerge.

Example 1. Site-Directed Editing of Maize Endogenous Gene ZmIPK Via the Pollen Tube Approach and the Shoot Apex Regeneration Approach I. Design of the Target Fragment: Target-C1

Target-C1:
(SEQ ID NO: 11)
5'-CCGAGCTCGACCACGCCGCCGAC-3';

(position 393-415 of the gene ZmIPK as shown in Genbank No. AY172635).

II. Preparation of pZmU3-gRNA Plasmid and pBUE411 Plasmid Containing C1 Site

C1 is the DNA sequence for the RNA that can complementarily bind to target-C1.

The following single-stranded oligonucleotides with sticky ends (underlined) were synthesized:

C1-1F:
(SEQ ID NO: 7)
5'-AGCAGTCGGCGGCGTGGTCGAGCT-3';

C1-2F:
(SEQ ID NO: 8)
5'-GGCGGTCGGCGGCGTGGTCGAGCT-3';

C1R:
(SEQ ID NO: 12)
5'-AAACAGCTCGACCACGCCGCCGAC-3'.

Double-stranded DNA with sticky ends was formed through annealing between C1-1F/C1R, and inserted between the two BbsI restriction sites in pZmU3-gRNA plasmid, resulting in a pZmU3-gRNA plasmid containing C1 site. The positive plasmid was verified by sequencing. A recombinant plasmid, which was obtained by inserting the DNA fragment as shown in 5'-AGCAGTCGGCGGCGTGGTCGAGCT-3' (SEQ ID NO: 7) in forward direction at the BbsI restriction site of pZmU3-gRNA plasmid, was positive, and designated as pZmU3-gRNA-C1.

Double-stranded DNA with sticky ends was formed through annealing between C1-2F/C1R, and inserted between the two BsaI restriction sites in pBUE411 plasmid, resulting in a pBUE411 plasmid containing C1 site. The positive plasmid was verified by sequencing. A recombinant plasmid, which was obtained by inserting the DNA fragment as shown in 5'-GGCGGTCGGCGGCGTGGTCGAGCT-3' (SEQ ID NO: 8) in forward direction at the BsaI restriction site of pBUE411 plasmid, was positive, and designated as pBUE411-C1.

III. Delivering the gRNA:Cas9 System into Maize Protoplast

The pJIT163-Ubi-Cas9 vector and the pZmU3-gRNA-C1 plasmid obtained in step II were introduced into the protoplast of maize protoplast. The specific process includes:

1. Growth of Maize Seedling

Seeds of maize hybrid variety HiII and inbred lines B73 and Zheng58 were soaked in water overnight, and transferred to a plate containing absorbent paper (water added), treated under light condition for 3 days for germination. The geminated maize seeds were grown in soil at 24° C. for 10-11 days, resulting in maize seedlings.

2. Isolation of Protoplast

1) Tender leaves of maize were taken, and the middle part thereof was cut into 0.5-1 mm threads using a cutter blade, placed into 50 ml enzymolysis solution for 5 h of digestion (0.5 h enzymolysis in vacuum, then 4.5 h slow shaking at 10 rpm).

Note: The temperature during enzymolysis should be kept between 20-25° C., the reaction should be carried out in the dark; and the solution should be gently shaken after the reaction so as to release the protoplasts.

2) the enzymolysis product was diluted by adding 30 ml of W5, and filtrated into a 50 ml round bottom centrifuge tube using a 75 μm Nylon filter membrane.

Note: The Nylon filter membrane should be submerged in 75% (volume percentage) ethanol, washed with water and then soaked in W5 for 2 min before use.

3) 23° C., 150 g centrifugation for 3 min, and the supernatant was discarded.

4) the pellet was suspended with 10 ml W5, centrifuged at 150 g for 3 min, and the supernatant was discarded.

5) the protoplasts were suspended by adding a proper amount of MMG solution, placed on ice until transformation.

Note: The concentration of the protoplasts needs to be determined by microscopy (×100). The amount of protoplasts was $2\times10^5$/ml to $1\times10^6$/ml.

3. Transformation of Maize Protoplast 1) 10 μg pJIT163-2NLSCas9 vector and 10 μg pZmU3-gRNA-C1 plasmid were added into a 2 ml centrifuge tube. 200 μl of the protoplast was added using a pipette and then mixed by gentle patting, kept still for 3-5 min. Then 220 μl of PEG4000 solution was added and mixed by gentle patting. Transformation was performed in dark for 15 min;

2) 880 μl W5 (room temperature) was added and mixed by reversing, 100 g centrifugation for 3 min, and the supernatant was discarded;

3) 1 ml WI solution was added and mixed by reversing, the content was gently transferred to a 6-well plate (with pre-added 1 ml WI solution), and then cultured at 23° C. overnight.

IV. Using PCR/RE Experiments to Analyze the Mutagenesis of Maize Endogenous Gene ZmIPK Using gRNA:Cas9 System 48 hours after the transformation of maize protoplast, genome DNA was extracted, which was used as template for PCR/RE (Polymerase Chain Reaction/Restriction digestion) experiment analysis. At the same time, the protoplasts of wild-type maize variety Hi II were used as a control. PCR/RE analysis method is based on Shan, Q. et al. Rapid and efficient gene modification in rice and Brachypodium using TALENs. Molecular Plant (2013). Since the target fragment (positions 393-415 of Genbank No. AY172635) of maize endogenous gene ZmIPK (Genbank No. AY172635) contains the recognition sequence (5'-GAGCTC-3') of restriction endonuclease SacI, and thus the restriction endonuclease SacI was used in the experiment for conducting the PCR/RE test. Primers used in the PCR amplification were:

```
ZmIPK-1F:
                                        (SEQ ID NO: 13)
5'-TCGCAGCCCCTGGCAGAGCAA-3';

ZmIPK-1R:
                                        (SEQ ID NO: 14)
5'-GAGACCTGGGAGAAGGAGACGGATCC-3'.
```

The results of PCR/RE experiments can be seen in FIG. 1, and the results showed that: mutations occurred at the target site of ZmIPK gene, the uncut bands was recovered and sequenced, and the sequencing results showed that insertion/deletion (indel) occurred at the target site of ZmIPK gene.

V. Site-Directed Editing of Maize Endogenous Gene ZmIPK Via the Pollen Tube Approach Cell-penetrating peptides (CPPs) are a class of short peptides which can carry macromolecules (including protein and nucleic acid) into the cells. Recent study shows that cell-penetrating peptides, when binding to DNA, can protect the DNA against enzymatic degradation. Therefore, cell-penetrating peptides are commonly used in the pollen tube approach so as to improve the efficiency.

1) Preparation of the DNA solution containing CPPs: solid powder CPPs (amino acid sequence: RKKRRQRRRRKKRRQRRR (SEQ ID NO: 15), synthesized by Shanghai Bio-engineering Co., Ltd.) were formulated into a 30 mg/ml stock solution with sterile water. CPPs were added into a mixture of pZmU3-gRNA-C1 plasmid and pJIT163-Ubi-Cas9 plasmid (the weight ratio of pZmU3-gRNA-C1 and pJIT163-Ubi-Cas9 in the mixture is 1:1) at a weight ratio of 1:1, such that the final concentrations of DNA and CPPs are 25-30 μg/ml (the final concentration of sum of the two plasmid is 25-30 μg/ml, the final concentration of CPPs is 25-30 μg/ml).

2) Strong maize plants (HiII, B73 and Zheng 58) in the field were selected as the recipient materials. After flowering, the stigmas of these plants were bagged to avoid cross or self-fertilization. The hand-pollinate was conducted at the right time. 18-21 hr post pollination, bags were removed, and filaments and bracts were cut, with a length of 2-3 cm from the top of the cob retained. The cut section of filaments is slightly lower than that of bracts, forming a small groove between filaments and bracts, in which 300-400 ul DNA solution from step 1) was dripped quickly with pipette. The filaments were immersed by DNA solution and the stigmas were bagged again. Each experiment was carried out in 40-50 corn cobs. After the grains mature, the corn cobs were harvested and dry individually.

3) The dried seeds were grown, and ZmIPK gene mutants were detected with the PCR/RE method (specific steps and the primers as used can be seen in IV) after germination.

Mutants were obtained via the pollen tube approach for maize plants of different genotypes. Detection results of some mutants are shown in FIGS. 2-4, indicating mutations occurred within the target site of ZmIPK gene in various maize varieties. Uncut bands were recovered and sequenced, and the sequencing results showed that insertion/deletion (indel) occurred at the target site of ZmIPK gene. It can be seen that mutants can be obtained at the whole plant level via the pollen tube approach as provided in the present invention, which is independent of the genotype or recipient.

VI. Site-Directed Editing of Maize Endogenous Gene ZmIPK Via the Shoot Apex Regeneration Approach

1. Preparation of the Maize Materials

1) Seeds of maize inbred line HiII were placed into a triangular flask, sterilized with 70% (v/v) alcohol for 5 min and 5% (v/v) sodium hypochlorite for 30 min, then washed in sterile water for 5 times. 1.5 volume of water was added and the flask was sealed and incubated at 28° C. for 4-6 h.

2) Second sterilization. The seeds were sterilized with 5% (v/v) sodium hypochlorite for 30 min, and then washed in sterile water for 5 times.

3) The sterilized seeds were placed on a sterilized plate with filter paper, incubated at 28° C. in dark for 3-4 days for germination. Germinated seeds with synchronous growth were transferred onto MS medium and cultured at 28° C. in dark for 3-4 days until the seedlings reached 4-5 cm.

2. Regeneration of Maize Shoot Apex

1) Cutting the buds: the stem was cut transversely at 1.5-2 mm above the joints, exposing the bud inside the stem. Then the bud was cut in the middle longitudinally to 0.2 mm below the joints (or just through the joints). About 0.8 mm root was retained.

2) pBUE411-C1 plasmid containing C1 was transformed into *Agrobacterium* competent cell AGL1. After verification by PCR and restriction digestion, a positive strain was used for infecting the plants.

3) Positive strain was plated onto LB solid medium, cultured at 28° C. in dark for 2 days. A few bacteria were scraped into 20 ml MS liquid medium, cultured at 28° C. to about $OD_{600}$=0.8. Then 200 μM Acetosyringone was added.

4) The incised plants were placed in to a plate, with the incisions downward. The plate was placed slantingly (30-45° C.) into a Vacuum device; *Agrobacterium* solution was added to submerge the incisions so as to allow an infection of 20 min. During infection, evacuation was set for 10 min, with a pressure of 0.05 MP.

5) After infection, the plants were taken out from the *Agrobacterium* solution (excess *Agrobacterium* solution on the plants was removed using filter paper) and inserted into MS medium, cultured at 23° C. in the dark for 3 days.

6) After the co-culture, the materials were taken out and washed to remove the medium, and then grown into a pot (⅘ common soil, ⅕ vermiculite on top). After transplant, seedlings were cultured at 28° C. in dark for 2 days and then 7-10 days in light, and then grown under normal conditions until fructification. Maize seeds as obtained were grown and tested for the ZmIPK gene mutation via the PCR/RE method after germination.

The results indicate that mutations occurred in the target site of ZmIPK gene. Uncut bands were recovered for sequencing. The sequencing results indicate that insertion/deletion (indel) occurred in the ZmIPK gene.

VII. Determining Whether pZmU3-gRNA-C1 and pJIT163-Ubi-Cas9 are Present in the Maize Mutants Obtained Via the Pollen Tube Approach Two primer sets were designed according to the sequences of pZmU3-gRNA-C1 plasmid and pJIT163-Ubi-Cas9 plasmid, for amplifying the two plasmids respectively.

ZmU3-F/C1R Located Between ZmU3 and the Target Fragment:

```
ZmU3-F:
                                        (SEQ ID NO: 16)
5'-CTGCCAAGATCAACAGCAACCA-3';

C1R:
                                        (SEQ ID NO: 12)
5'-AAACAGCTCGACCACGCCGCCGAC-3'.
```

Theoretically, the amplified fragment should be about 322 bp, and the sequence should be positions 467-788 of SEQ ID NO:1. SEQ ID NO:1 is the sequence of pZmU3-gRNA-C1.

Cas9-1F/Cas9-1R Located on the pJIT163-Ubi-Cas9 Vector:

```
Cas9-1F:
                                        (SEQ ID NO: 17)
5'-CTTCCCAAGCATTCCCTCCTGT-3';

Cas9-1R:
                                        (SEQ ID NO: 18)
5'-CTTATGCCGTCCCATGACCTTC-3'.
```

Theoretically, the amplified fragment should be about 744 bp, and the sequence should be positions 1573-2316 of SEQ ID NO:2. SEQ ID NO:2 is the sequence of Cas9 in pJIT163-Ubi-Cas9.

No target bands were amplified for all the plants (FIG. 5), indicating that the present invention prevents the insertion or carrying of a transgene when performing site-directed modification to a plant, and the mutant as obtained have relatively high bio-safety.

VIII. Determining Whether pBUE411-C1 is Present in the Maize Mutants Obtained Via the Shoot Apex Regeneration Approach Two primer sets were designed according to the sequence of pBUE411-C1 plasmid, for amplifying OsU3p and Cas9 respectively.

pBUE411-1F/C1R Locate Between OsU3p and the Target Fragment:

```
pBUE411-1F:
                                        (SEQ ID NO: 19)
5'-GACAGGCGTCTTCTACTGGTGCTAC-3';

C1R:
                                        (SEQ ID NO: 12)
5'-AAACAGCTCGACCACGCCGCCGAC-3'.
```

Theoretically, the amplified fragment should be about 289 bp, and the sequence should be positions 174-462 of SEQ ID NO:3. SEQ ID NO:3 is the gRNA sequence of pBUE411-C1.

CAS9-2F/CAS9-2R Locate in Cas9 Region on the pBUE411-C1 Vector:

```
CAS9-2F:
                                        (SEQ ID NO: 20)
5'-CTCCCTAAGCACTCGCTCCTGT-3';

CAS9-2R:
                                        (SEQ ID NO: 21)
5'-TTCTGCGTGGTCTGATTCTCCC-3'.
```

Theoretically, the amplified fragment should be about 794 bp, and the sequence should be positions 1639-2432 of SEQ ID NO:4. SEQ ID NO:4 is the Cas9 sequence of pHSN411-C1.

No target bands were amplified for all the plants, indicating that the present invention prevents the insertion or carrying of a transgene when performing site-directed modification to a plant, and the mutant as obtained have relatively high bio-safety.

Example 2. Site-Directed Editing of *Arabidopsis* Endogenous Gene AtPTPA Via the Inflorescence-Dipping Approach I. Design of the Target Fragment: Target-C2

Target-C2:
(SEQ ID NO: 22)
5'-CCGACGATATCCGCCGATTTCAC-3';

(position 351-373 of the gene AtPTPA as shown in Genbank No. AF360133).

II. Preparation of pHSN401 Plasmid Containing C2 Fragment

C2 is the DNA sequence for the RNA that can complementarily bind to target-C2.

The following single-stranded oligonucleotides with sticky ends (underlined) were synthesized:

C2F:
(SEQ ID NO: 10)
5'-ATTGGTGAAATCGGCGGATATCGT-3';

C2R:
(SEQ ID NO: 23)
5'-AAACACGATATCCGCCGATTTCAC-3'.

Double-stranded DNA with sticky ends was formed through oligonucleotide annealing, and inserted between the two BsaI restriction sites in pHSN401 plasmid, resulting in a pHSN401 plasmid containing C2 site. The positive plasmid was verified by sequencing. A recombinant plasmid, which was obtained by inserting the DNA fragment as shown in 5'-ATTGGTGAAATCGGCGGATATCGT-3' (SEQ ID NO: 10) in forward direction at the BsaI restriction site of pHSN401 plasmid, was positive, and designated as pHSN401-C2.

III. Delivering the gRNA:Cas9 System into *Arabidopsis* Protoplast

The pHSN401-C2 plasmid obtained in step II was introduced into the protoplasts of *Arabidopsis* ecotype Columbia. The specific process includes:

1. Growth of *Arabidopsis* Seedling

1) Seed treatment: Seeds of *Arabidopsis* ecotype Columbia were placed into a 1.5 mL tube and soaked in 75% (v/v) alcohol for 1 min and 10% (v/v) sodium hypochlorite for 15 min, then washed in sterile water for 5-6 times.

2) The sterilized seeds were plated individually onto MS medium with a micropipette. The plates were sealed and placed under 4° C., 3-4 days for vernalization.

3) After vernalization, the plates were transferred into an incubator, cultured under the following conditions: 25±2° C., illuminance 5500±300Lx, 12 h light/d. After 3 week growth, seedlings were transplanted.

4) The seedlings were transplanted into soil (peat soil:vermiculite:pearlite=1:1:1) carefully, covered by a film for 3-4 days, and then cultured under 21° C., 6300±300 Lx.

2. Isolation of Protoplast

1) Tender leaves of *Arabidopsis* ecotype Columbia (grown for about 1 month) were taken, and cut into 0.5 mm threads using a cutter blade, placed into 50 ml enzymolysis solution for 5 h of digestion (0.5 h enzymolysis in vacuum, then 4.5 h slow shaking at 10 rpm).

Note: The temperature during enzymolysis should be kept between 20-25° C., the reaction should be carried out in the dark; and the solution should be gently shaken after the reaction so as to release the protoplasts.

2) the enzymolysis product was diluted by adding 30 ml of W5, and filtrated into a 50 ml round bottom centrifuge tube using a 75 μm Nylon filter membrane.

Note: The Nylon filter membrane should be submerged in 75% (volume percentage) ethanol, washed with water and then soaked in W5 for 2 min before use.

3) 23° C., 60 g centrifugation for 5 min, and the supernatant was discarded.

4) the pellet was resuspended with 10 ml W5 by gently shaking; 60 g centrifugation for 5 min, and the supernatant was discarded.

5) the protoplasts were suspended by adding a proper amount of MMG solution, placed on ice until transformation.

Note: The concentration of the protoplasts needs to be determined by microscopy (×100). The amount of protoplasts was $2 \times 10^5$/ml to $1 \times 10^6$/ml.

3. Transformation of *Arabidopsis* Protoplast 1) 20 μg pHSN401-C2 plasmid was added into a 2 ml centrifuge tube. 200 μl of the protoplast obtained in above step 2 was added using a pipette and then mixed by gentle patting. Then 250 μl of PEG4000 was added and mixed by gentle patting. Transformation was performed in dark for 15-30 min;

2) 880 μl W5 (room temperature) was added and mixed by reversing, 60 g centrifugation for 5 min, and the supernatant was discarded;

3) 1 ml W5 was added and mixed by reversing, the content was gently transferred to a 6-well plate (with pre-added 1 ml W5), and then cultured at 23° C. overnight.

IV. Using PCR/RE Experiments to Analyze the Site-Directed Mutagenesis of *Arabidopsis* Endogenous Gene AtPTPA Using gRNA:Cas9 System 48 hours after the transformation of *Arabidopsis* protoplast, genomic DNA was extracted, which was used as template for PCR/RE (Polymerase Chain Reaction/Restriction digestion) experiment analysis. PCR/RE analysis method is based on Shan, Q. et al. Rapid and efficient gene modification in rice and Brachypodium using TALENs. Molecular Plant (2013). Since the target fragment (positions 351-373 of Genbank No. AF360133) of *Arabidopsis* endogenous gene AtPTPA (Genbank No. AF360133) contains the recognition sequence (5'-GATATC-3') of restriction endonuclease EcoRV, and thus the restriction endonuclease EcoRV was used in the experiment for conducting the PCR/RE test. Primers used in the PCR amplification were:

PTPA-F:
(SEQ ID NO: 24)
5'-GATGCTCCAGCCACCATATC-3';

PTPA-R:
(SEQ ID NO: 25)
5'-CAGTTCGGTACACCACTTATATCA-3'.

The results of PCR/RE experiments can be seen in FIG. 6, and the results showed that: mutations occurred at the target site of AtPTPA gene, the uncut bands in FIG. 6 were recovered and sequenced, and the sequencing results showed that insertion/deletion (indel) occurred at the target site of AtPTPA gene.

V. Site-Directed Editing of *Arabidopsis* Endogenous Gene AtPTPA Via the Inflorescence-Dipping Approach 1) Preparation of the *Arabidopsis* materials The buds of *Arabidopsis* were removed at the first flowering to facilitate branching. Siliques were cut off before transformation by inflorescence-dipping.

2) pHSN401-C2 plasmid containing C2 was transformed into *Agrobacterium* competent cell GV3101. After verification by PCR and restriction digestion, positive strain was used for infecting the plants.

3) Positive *Agrobacterium* strain was cultured in a 2 ml tube for 8-10 hr, and then transferred to 200 ml LB medium (inoculated at a ratio of 1:100), cultured overnight to an $OD_{600}$ of about 0.8~1.0. *Agrobacterium* cells were collected by centrifuging for 15 min, and resuspended in infection buffer (2.16 g/L MgCl2.6H$_2$O, 5% sucrose, 0.02% silwet L-77) for infecting the plants.

4) The inflorescences of *Arabidopsis* were dipped into 100 ml infection buffer contained in a big plate for 2 min, continually rotating the plants. After infection, excess *Agrobacterium* solution on the plants was removed using filter paper. The plants were covered by a black plastic bag or film for 24 hr cultivation in dark. As the flowering period of *Arabidopsis* is relatively long, it generally requires 2-3 infections.

5) Plants were grown under normal conditions. T1 seeds were harvested and grown. After germination, AtPTPA gene was tested using PCR/RE (specific steps and the primers as used can be seen in IV). In the 500 plants as obtained, 20 are mutants of AtPTPA gene. Wild type *Arabidopsis* ecotype Columbia was set as a control.

The results were shown in FIG. 7, and the results indicated that mutations occurred at the target site of AtPTPA gene, the uncut bands in FIG. 7 were recovered and sequenced, and the sequencing results showed that insertion/deletion (indel) occurred at the target site of AtPTPA gene.

6) PCR applications were performed against the 20 mutants as obtained in 5) to determine whether pHSN401-C2 is present in the mutants. 2 primer sets were designed for the amplification (target to U6-26p and Cas9, respectively).

pHSN401-1F/C2R Locate Between U6-26p and the Target Fragment:

pHSN401-1F:
(SEQ ID NO: 26)
5'-TGTCCCAGGATTAGAATGATTAGGC-3';

C2R:
(SEQ ID NO: 27)
5'-AAACACGATATCCGCCGATTTCAC-3'.

Theoretically, the amplified fragment should be about 286 bp, and the sequence should be positions 170-455 of SEQ ID NO:5. SEQ ID NO:5 is the partial sequence of gDNA in pHSN401-C2.

CAS9-2F/CAS9-2R Locate in Cas9 Region of pHSN401-C2 Vector:

CAS9-2F:
(SEQ ID NO: 20)
5'-CTCCCTAAGCACTCGCTCCTGT-3';

CAS9-2R:
(SEQ ID NO: 21)
5'-TTCTGCGTGGTCTGATTCTCCC-3'.

Theoretically, the amplified fragment should be about 794 bp, and the sequence should be positions 1639-2432 of SEQ ID NO:4. SEQ ID NO:4 is the Cas9 sequence in pHSN401-C2.

The gel electrophoretogram of the amplification of *Arabidopsis* AtPTPA gene mutant using primers pHSN401-1F/C2R on pHSN401-C2 is shown in FIG. 8*a*. The gel electrophoretogram of the amplification of *Arabidopsis* AtPTPA gene mutant using primers CAS9-2F/CAS9-2R on pHSN401-C2 is shown in FIG. 8*b*. It can be seen that, no target bands were amplified in the *Arabidopsis* AtPTPA gene mutants as obtained in 5), indicating there is no fragment of the gDNA: Cas9 system present in the mutants.

7) 9 plants were randomly selected from the progeny of the 20 mutants obtained in 5) for PCR/RE analysis and the results were shown in FIG. 9. It can be seen that the *Arabidopsis* AtPTPA gene mutation as obtained can be stably transmitted to the progeny. Therefore, the present invention prevents the insertion or carrying of a transgene when performing site-directed modification to a plant, which avoids the public concerns about the safety of transgenic product, and also avoids the tissue culture process.

The invention claimed is:

1. A method for conducting site-directed modification to a target fragment of a target gene in a whole plant, comprising:

transiently expressing a sequence-specific nuclease in said plant, wherein the sequence-specific nuclease is a CRISPR/Cas9 nuclease, wherein a whole plant is used as the subject for transient expression, and wherein said sequence-specific nuclease targets and cleaves said target fragment, whereby the site-directed modification is achieved via the self DNA repairing of said plant, wherein the method for transiently expressing said site-directed nuclease in said plant comprises the following steps:

a) delivering the sequence-specific nuclease or a genetic material for expressing the sequence-specific nuclease into a part of said plant selected from the group consisting of a pollen tube, inflorescence, shoot apex, or ovary, and b) growing the plant obtained in step a) in the absence of selection pressure, wherein the sequence-specific nuclease or the genetic material not integrated into the plant chromosome is degraded, wherein step b) does not comprise tissue culture, wherein said genetic material is a recombinant vector or a DNA linear fragment or an in vitro transcribed RNA, and wherein when said plant part is a pollen tube, the plant is selected from the group consisting of maize, wheat, soybean, cotton, and tobacco, and the delivery is performed by injecting a solution containing cell-penetrating peptides and said recombinant vector or DNA linear fragment or in vitro transcribed RNA or a solution containing cell-penetrating peptides and said sequence-specific nuclease into the stigma after pollination;

wherein when said plant part is an inflorescence, the plant is selected from the group consisting of *Arabidopsis*, wheat, and rye, and the delivery is performed by dipping the inflorescence in a solution of *Agrobacterium tumefaciens* carrying said recombinant vector or DNA linear fragment and subsequently cultivating the inflorescence covered and in the dark;

wherein when said plant part is a shoot apex, the plant is selected from the group consisting of maize, *Rosa roxbunghii, Eriobotrya japonica, Carica papaya*, and *Rosa canina*, and the delivery is performed by dipping the shoot apex in a solution of *Agrobacterium tumefaciens* carrying said recombinant vector or DNA linear fragment under evacuation; or wherein when said plant part is an ovary, the plant is selected from the group consisting of wheat, soybean, cotton, and *Dendrobium nobile* Lindt, and the delivery is performed by injecting a solution containing said recombinant vector or DNA linear fragment or in vitro transcribed RNA or a solution containing said sequence-specific nuclease into the ovary after pollination, or by injecting a solution of *Agrobacterium tumefaciens* carrying said recombinant vector or DNA linear fragment into the ovary after pollination.

2. The method of claim 1, wherein the genetic material is composed of:

a recombinant vector or DNA fragment capable of transcribing guide RNA and expressing Cas9 protein;

a recombinant vector or DNA fragment capable of transcribing guide RNA and a recombinant vector or DNA fragment or RNA capable of expressing Cas9 protein; or a guide RNA and a recombinant vector or DNA fragment or RNA capable of expressing Cas9 protein, and wherein the guide RNA is an RNA with a palindromic structure which is formed by partial base-pairing between crRNA and tracrRNA and the crRNA contains an RNA fragment that can complementarily bind to the target fragment.

3. The method of claim 1, wherein the site-directed modification is an insertion, deletion, and/or replacement mutation in the target fragment.

4. A method for making a transgene-free mutant plant comprising performing site-directed modification to a target fragment of a target gene in a plant of interest according to the method of claim 1 so as to obtain a plant in which a function of the target gene is lost and the genome of the plant is free of integrated exogenous genes.

5. The method of claim 1, wherein said plant is a plant of any genotype.

6. The method of claim 1, wherein said plant is maize, the sequence-specific nuclease is a CRISPR/Cas9 nuclease, and the target gene is ZmIPK.

* * * * *

SEQUENCE LISTING

```
<160> NUMBER OF SEQ ID NOS: 47

<210> SEQ ID NO 1
<211> LENGTH: 883
<212> TYPE: DNA
<213> ORGANISM: Artificial
<220> FEATURE:
<223> OTHER INFORMATION: pZmU3-gRNA-C1

<400> SEQUENCE: 1
gaattccatc taagtatctt ggtaaagcat ggattaattt ggatgcccac ttcaggtcta      60
tgcagctccg gtgccttgtg attgtgagtt gtgaccgatg ctcatgctat tctgcatttc     120
tgcgatgtat gtagctagta gatcttcaaa actaacaccg catgccatca tcatccactg     180 cttgattta gtctcaccgc tggccaaaaa tgtgatgatg ccagaaacct caactacctt     240
gaatcaacac gggcccaaca gtgtgatgac gacagaaaca aaaaaaaatg agccaatagt     300
tcagaaggag gcactatgca gaaactacat ttctgaaggt gactaaaagg tgagcgtaga     360
```

```
gtgtaattac tagtagttta gccaccatta cccaaatgct ttcgagcttg tattaagatt    420
tcctaagctg agcatcatca ctgatctgca ggccaccctc gcttcgctgc caagatcaac    480
agcaaccatg tggcggcaac atccagcatt gcacatgggc taaagattga gctttgtgcc    540
tcgtctaggg atcagctgag gttatcagtc tttccttttt ttcatccagg tgaggcatca    600
agctactact gcctcgattg gctggacccg aagcccacat gtaggatacc agaatgggcc    660
gacccaggac gcagtatgtt ggccagtccc accggttagt gccatctcgg ttgctcacat    720
gcgtagaagc cagcttaaaa atttagcttt ggtgactcac agcagtcggc ggcgtggtcg    780
agctgtttta gagctagaaa tagcaagtta aaataaggct agtccgttat caacttgaaa    840
aagtggcacc gagtcggtgc ttttttggt accggatcct acg    883
```

```
<210> SEQ ID NO 2
<211> LENGTH: 4206
<212> TYPE: DNA
<213> ORGANISM: Artificial
<220> FEATURE:
<223> OTHER INFORMATION: Cas9 sequence in pJIT163-Ubi-Cas9

<400> SEQUENCE: 2
atggccccta agaagaagag aaaggtcggt attcacggcg ttcctgcggc gatggacaag     60
aagtatagta ttggtctgga cattgggacg aattccgttg gctgggccgt gatcaccgat    120
gagtacaagg tcccttccaa gaagtttaag gttctgggga acaccgatcg gcacagcatc    180
aagaagaatc tcattggagc cctcctgttc gactcaggcg agaccgccga agcaacaagg    240
ctcaagagaa ccgcaaggag acggtataca agaaggaaga ataggatctg ctacctgcag    300
gagattttca gcaacgaaat ggcgaaggtg gacgattcgt tctttcatag attggaggag    360
agtttcctcg tcgaggaaga taagaagcac gagaggcatc ctatctttgg caacattgtc    420
gacgaggttg cctatcacga aaagtacccc acaatctatc atctgcggaa gaagcttgtg    480
gactcgacta taaggcgga ccttagatta atctacctcg ctctggcaca catgattaag    540
ttcaggggcc atttttctgat cgaggggat cttaacccgg acaatagcga tgtggacaag    600
ttgttcatcc agctcgtcca aacctacaat cagctctttg aggaaaaccc aattaatgct    660
tcaggcgtcg acgccaaggc gatcctgtct gcacgccttt caaagtctcg ccggcttgag    720
aacttgatcg ctcaactccc gggcgaaaag aagaacggct tgttcgggaa tctcattgca    780
ctttcgttgg ggctcacacc aaacttcaag agtaattttg atctcgctga ggacgcaaag    840
ctgcagcttt ccaaggacac ttatgacgat gacctggata ccttttggcc caaatcggc    900 gatcagtacg cggacttgtt cctcgccgcg aagaatttgt cggacgcgat cctcctgagt    960
gatattctcc gcgtgaacac cgagattaca aaggcccgc tctcggcgag tatgatcaag    1020
cgctatgacg agcaccatca ggatctgacc cttttgaagg ctttggtccg gcagcaactc    1080
ccagagaagt acaaggaaat cttctttgat caatccaaga acggctacgc tggttatatt    1140
gacggcgggg catcgcagga ggaattctac aagtttatca gccaattct ggagaagatg    1200 gatggcacag aggaactcct ggtgaagctc aatagggagg accttttgcg gaagcaaaga    1260
actttcgata cggcagcat ccctcaccag attcatctcg gggagctgca cgccatcctg    1320
agaaggcagg aagacttcta ccccttcttt aaggataacc gggagaagat cgaaaagatt    1380
ctgacgttca gaattccgta ctatgtcgga ccactcgccc ggggtaattc cagatttgcg    1440
tggatgacca gaaagagcga ggaaaccatc acaccttgga acttcgagga agtggtcgat    1500
aagggcgctt ccgcacagag cttcattgag cgcatgacaa attttgacaa gaacctgcct    1560
```

```
aatgagaagg tccttcccaa gcattccctc ctgtacgagt atttcactgt ttataacgaa   1620
ctcacgaagg tgaagtatgt gaccgaggga atgcgcaagc ccgccttcct gagcggcgag   1680
caaaagaagg cgatcgtgga ccttttgttt aagaccaatc ggaaggtcac agttaagcag   1740
ctcaaggagg actacttcaa gaagattgaa tgcttcgatt ccgttgagat cagcggcgtg   1800
gaagacaggt ttaacgcgtc actggggact taccacgatc tcctgaagat cattaaggat   1860
aaggacttct tggacaacga ggaaaatgag gatatcctcg aagacattgt cctgactctt   1920
acgttgtttg aggataggga aatgatcgag gaacgcttga agacgtatgc ccatctcttc   1980
gatgacaagg ttatgaagca gctcaagaga agaagataca ccggatgggg aaggctgtcc   2040
cgcaagctta tcaatggcat tagagacaag caatcaggga agacaatcct tgacttttg    2100 aagtctgatg gcttcgcgaa caggaatttt atgcagctga ttcacgatga ctcacttact   2160
ttcaaggagg atatccagaa ggctcaagtg tcgggacaag gtgacagtct gcacgagcat   2220
atcgccaacc ttgcgggatc tcctgcaatc aagaagggta ttctgcagac agtcaaggtt   2280
gtggatgagc ttgtgaaggt catgggacgg cataagcccg agaacatcgt tattgagatg   2340
gccagagaaa atcagaccac acaaaagggt cagaagaact cgaggagcg catgaagcgc    2400 atcgaggaag gcattaagga gctggggagt cagatcctta aggagcaccc ggtggaaaac   2460
acgcagttgc aaaatgagaa gctctatctg tactatctgc aaaatggcag ggatatgtat   2520
gtggaccagg agttggatat taaccgcctc tcggattacg acgtcgatca tatcgttcct   2580
cagtccttcc ttaaggatga cagcattgac aataaggttc tcaccaggtc cgacaagaac   2640
cgcgggaagt ccgataatgt gcccagcgag gaagtcgtta agaagatgaa gaactactgg   2700
aggcaacttt tgaatgccaa gttgatcaca cagaggaagt ttgataacct cactaaggcc   2760
gagcgcggag gtctcagcga actggacaag gcgggcttca ttaagcggca actggttgag   2820
actagacaga tcacgaagca cgtggcgcag attctcgatt cacgcatgaa cacgaagtac   2880
gatgagaatg acaagctgat ccgggaagtg aaggtcatca ccttgaagtc aaagctcgtt   2940
tctgacttca ggaaggattt ccaattttat aaggtgcgcg agatcaacaa ttatcaccat   3000
gctcatgacg catacctcaa cgctgtggtc ggaacagcat tgattaagaa gtacccgaag   3060
ctcgagtccg aattcgtgta cggtgactat aaggtttacg atgtgcgcaa gatgatcgcc   3120
aagtcagagc aggaaattgg caaggccact gcgaagtatt tcttttactc taacattatg   3180
aatttctttt agactgagat cacgctggct aatggcgaaa tccggaagag accacttatt   3240
gagaccaacg gcgagacagg ggaaatcgtg tgggacaagg ggagggattt cgccacagtc   3300
cgcaaggttc tctctatgcc tcaagtgaat attgtcaaga agactgaagt ccagacgggc   3360
gggttctcaa aggaatctat tctgcccaag cggaactcgg ataagcttat cgccagaaag   3420
aaggactggg acccgaagaa gtatggaggt ttcgactcac caacggtggc ttactctgtc   3480
ctggttgtgg caaaggtgga gaaggaaaag tcaaagaagc tcaagtctgt caaggagctc   3540
ctgggtatca ccattatgga gaggtccagc ttcgaaaaga tccgatcga ttttctcgag     3600 gcgaagggat ataaggaagt gaagaaggac ctgatcatta agcttccaaa gtacagtctt   3660
ttcgagttgg aaaacggcag gaagcgcatg ttggcttccg caggagagct ccagaagggt   3720
aacgagcttg ctttgccgtc caagtatgtg aacttcctct atctggcatc ccactacgag   3780
aagctcaagg gcagcccaga ggataacgaa cagaagcaac tgtttgtgga gcaacacaag   3840
cattatcttg acgagatcat tgaacagatt tcggagttca gtaagcgcgt catcctcgcc   3900
```

| | |
|---|---|
| gacgcgaatt tggataaggt tctctcagcc tacaacaagc accgggacaa gcctatcaga | 3960 |
| gagcaggcgg aaaatatcat tcatctcttc accctgacaa accttgggc tcccgctgca | 4020 |
| ttcaagtatt ttgacactac gattgatcgg aagagataca cttctacgaa ggaggtgctg | 4080 |
| gatgcaaccc ttatccacca atcgattact ggcctctacg agacgcggat cgacttgagt | 4140 |
| cagctcgggg gggataagag accagcggca accaagaagg caggacaagc gaagaagaag | 4200 |
| aagtag | 4206 |

<210> SEQ ID NO 3
<211> LENGTH: 544
<212> TYPE: DNA
<213> ORGANISM: Artificial
<220> FEATURE:
<223> OTHER INFORMATION: gRNA sequence of pBUE411-C1

<400> SEQUENCE: 3

| | |
|---|---|
| agtaattcat ccaggtctcc aagttctagg attttcagaa ctgcaactta ttttatcaag | 60 |
| gaatctttaa acatacgaac agatcactta aagttcttct gaagcaactt aaagttatca | 120 |
| ggcatgcatg gatcttggag gaatcagatg tgcagtcagg gaccatagca caagacaggc | 180 |
| gtcttctact ggtgctacca gcaaatgctg gaagccggga acactgggta cgttggaaac | 240 |
| cacgtgatgt gaagaagtaa gataaactgt aggagaaaag catttcgtag tgggccatga | 300 |
| agcctttcag gacatgtatt gcagtatggg ccggcccatt acgcaattgg acgacaacaa | 360 |
| agactagtat tagtaccacc tcggctatcc acatagatca aagctgattt aaaagagttg | 420 |
| tgcagatgat ccgtggcggt cggcggcgtg gtcgagctgt tttagagcta gaaatagcaa | 480 |
| gttaaaataa ggctagtccg ttatcaactt gaaaaagtgg caccgagtcg gtgcttttttt | 540 |
| tttt | 544 |

<210> SEQ ID NO 4
<211> LENGTH: 4272
<212> TYPE: DNA
<213> ORGANISM: Artificial
<220> FEATURE:
<223> OTHER INFORMATION: Cas9 sequence of pHSN411-C1

<400> SEQUENCE: 4

| | |
|---|---|
| atggattaca aggaccacga cgggattac aaggaccacg acattgatta caaggatgat | 60 |
| gatgacaaga tggctccgaa gaagaagagg aaggttggca tccacggggt gccagctgct | 120 |
| gacaagaagt actcgatcgg cctcgatatt gggactaact ctgttggctg gccgtgatc | 180 |
| accgacgagt acaaggtgcc ctcaaagaag ttcaaggtcc tgggcaacac cgatcggcat | 240 |
| tccatcaaga gaatctcat ggcgctctc ctgttcgaca cggcgagac ggctgaggct | 300 |
| acgcggctca gcgcaccgc ccgcaggcgg tacacgcgca ggaagaatcg catctgctac | 360 |
| ctgcaggaga ttttctccaa cgagatggcg aaggttgacg attctttctt ccacaggctg | 420 |
| gaggagtcat tcctcgtgga ggaggataag aagcacgagc ggcatccaat cttcggcaac | 480 |
| attgtcgacg aggttgccta ccacgagaag taccctacga tctaccatct gcggaagaag | 540 |
| ctcgtggact ccacagataa ggcggacctc cgcctgatct acctcgctct ggcccacatg | 600 |
| attaagttca ggggccattt cctgatcgag ggggatctca acccggacaa tagcgatgtt | 660 |
| gacaagctgt tcatccagct cgtgcagacg tacaaccagc tcttcgagga aaccccatt | 720 |
| aatgcgtcag gcgtcgacgc gaaggctatc ctgtccgcta ggctctcgaa gtctcggcgc | 780 |
| ctcgagaacc tgatcgccca gctgccgggc gagaagaaga acggcctgtt cgggaatctc | 840 |

```
attgcgctca gcctggggct cacgcccaac ttcaagtcga atttcgatct cgctgaggac     900
gccaagctgc agctctccaa ggacacatac gacgatgacc tggataacct cctggcccag     960
atcggcgatc agtacgcgga cctgttcctc gctgccaaga atctgtcgga cgccatcctc    1020
ctgtctgata ttctcagggt gaacaccgag attacgaagg ctccgctctc agcctccatg    1080
atcaagcgct acgacgagca ccatcaggat ctgaccctcc tgaaggcgct ggtcaggcag    1140
cagctccccg agaagtacaa ggagatcttc ttcgatcagt cgaagaacgg ctacgctggg    1200
tacattgacg gcggggcctc tcaggaggag ttctacaagt tcatcaagcc gattctggag    1260
aagatggacg gcacggagga gctgctggtg aagctcaatc gcgaggacct cctgaggaag    1320
cagcggacat cgataacgg cagcatccca caccagattc atctcgggga gctgcacgct    1380
atcctgagga ggcaggagga cttctaccct ttcctcaagg ataaccgcga agatcgag      1440 aagattctga ctttcaggat cccgtactac gtcggcccac tcgctagggg caactcccgc    1500
ttcgcttgga tgacccgcaa gtcagaggag acgatcacgc cgtggaactt cgaggaggtg    1560
gtcgacaagg gcgctagcgc tcagtcgttc atcgagagga tgacgaattt cgacaagaac    1620
ctgccaaatg agaaggtgct ccctaagcac tcgctcctgt acgagtactt cacagtctac    1680
aacgagctga ctaaggtgaa gtatgtgacc gagggcatga ggaagccggc tttcctgtct    1740
ggggagcaga agaaggccat cgtggacctc ctgttcaaga ccaaccggaa ggtcacggtt    1800
aagcagctca aggaggacta cttcaagaag attgagtgct tcgattcggt cgagatctct    1860
ggcgttgagg accgcttcaa cgcctccctg gggacctacc acgatctcct gaagatcatt    1920
aaggataagg acttcctgga caacgaggag aatgaggata tcctcgagga cattgtgctg    1980
acactcactc tgttcgagga ccgggagatg atcgaggagc gcctgaagac ttacgcccat    2040
ctcttcgatg acaaggtcat gaagcagctc aagaggagga ggtacaccgg ctgggggagg    2100
ctgagcagga agctcatcaa cggcattcgg acaagcagt ccgggaagac gatcctcgac     2160
ttcctgaaga gcgatggctt cgcgaaccgc aatttcatgc agctgattca cgatgacagc    2220
ctcacattca aggaggatat ccagaaggct caggtgagcg ccagggga ctcgctgcac      2280 gagcatatcg cgaacctcgc tggctcgcca gctatcaaga aggggattct gcagaccgtg    2340
aaggttgtgg acgagctggt gaaggtcatg ggcaggcaca agcctgagaa catcgtcatt    2400
gagatggccc gggagaatca gaccacgcag aagggccaga gaactcacg cgagaggatg     2460 aagaggatcg aggagggcat taaggagctg gggtcccaga tcctcaagga gcacccggtg    2520
gagaacacgc agctgcagaa tgagaagctc tacctgtact acctccagaa tggccgcgat    2580
atgtatgtgg accaggagct ggatattaac aggctcagcg attacgacgt cgatcatatc    2640
gttccacagt cattcctgaa ggatgactcc attgacaaca aggtcctcac caggtcggac    2700
aagaaccggg gcaagtctga taatgttcct tcagaggagg tcgttaagaa gatgaagaac    2760
tactggcgcc agctcctgaa tgccaagctg atcacgcagc ggaagttcga taacctcaca    2820
aaggctgaga ggggcgggct ctctgagctg acaaggcgg cttcatcaa gaggcagctg      2880 gtcgagacac ggcagatcac taagcacgtt gcgcagattc tcgactcacg gatgaacact    2940
aagtacgatg agaatgacaa gctgatccgc gaggtgaagg tcatcaccct gaagtcaaag    3000
ctcgtctccg acttcaggaa ggatttccag ttctacaagg ttcgggagat caacaattac    3060
caccatgccc atgacgcgta cctgaacgcg gtggtcggca cagctctgat caagaagtac    3120
ccaaagctcg agagcgagtt cgtgtacggg gactacaagg tttacgatgt gaggaagatg    3180
```

```
atcgccaagt cggagcagga gattggcaag gctaccgcca agtacttctt ctactctaac    3240
attatgaatt tcttcaagac agagatcact ctggccaatg gcgagatccg gaagcgcccc    3300
ctcatcgaga cgaacggcga gacggggggag atcgtgtggg acaagggcag ggatttcgcg    3360
accgtcagga aggttctctc catgccacaa gtgaatatcg tcaagaagac agaggtccag    3420
actggcgggt tctctaagga gtcaattctg cctaagcgga acagcgacaa gctcatcgcc    3480
cgcaagaagg actgggatcc gaagaagtac ggcgggttcg acagcccac tgtggcctac     3540 tcggtcctgg ttgtggcgaa ggttgagaag ggcaagtcca agaagctcaa gagcgtgaag    3600
gagctgctgg ggatcacgat tatggagcgc tccagcttcg agaagaaccc gatcgatttc    3660
ctggaggcga agggctacaa ggaggtgaag aaggacctga tcattaagct ccccaagtac    3720
tcactcttcg agctggagaa cggcaggaag cggatgctgg cttccgctgg cgagctgcag    3780
aaggggaacg agctggctct gccgtccaag tatgtgaact tcctctacct ggcctccac     3840 tacgagaagc tcaagggcag ccccgaggac aacgagcaga agcagctgtt cgtcgagcag    3900
cacaagcatt acctcgacga gatcattgag cagatttccg agttctccaa gcgcgtgatc    3960
ctggccgacg cgaatctgga taaggtcctc tccgcgtaca acaagcaccg cgacaagcca    4020
atcagggagc aggctgagaa tatcattcat ctcttcaccc tgacgaacct cggcgccct    4080 gctgctttca gtacttcga cacaactatc gatcgcaaga ggtacacaag cactaaggag    4140
gtcctggacg cgaccctcat ccaccagtcg attaccggcc tctacgagac gcgcatcgac    4200
ctgtctcagc tcgggggcga caagcggcca gcggcgacga agaaggcggg gcaggcgaag    4260
aagaagaagt ga                                                        4272

<210> SEQ ID NO 5
<211> LENGTH: 487
<212> TYPE: DNA
<213> ORGANISM: Artificial
<220> FEATURE:
<223> OTHER INFORMATION: partial gDNA sequence of pHSN401-C2

<400> SEQUENCE: 5
aagcttcgac ttgccttccg cacaatacat catttcttct tagcttttt tcttcttctt      60 cgttcataca gttttttttt gtttatcagc ttacattttc ttgaaccgta gctttcgttt    120
tcttcttttt aactttccat tcggagtttt tgtatcttgt ttcatagttt gtcccaggat    180
tagaatgatt aggcatcgaa ccttcaagaa tttgattgaa taaaacatct tcattcttaa    240
gatatgaaga taatcttcaa aaggcccctg ggaatctgaa agaagagaag caggcccatt    300
tatatgggaa agaacaatag tatttcttat ataggcccat ttaagttgaa acaatcttc     360 aaaagtccca catcgcttag ataagaaaac gaagctgagt ttatatacag ctagagtcga    420
agtagtgatt ggtgaaatcg gcggatatcg tgttttagag ctagaaatag caagttaaaa    480
taaggct                                                              487

<210> SEQ ID NO 6
<211> LENGTH: 20
<212> TYPE: DNA
<213> ORGANISM: Zea mays

<400> SEQUENCE: 6
agctcgacca cgccgccgac                                                 20

<210> SEQ ID NO 7
<211> LENGTH: 24
```

```
<212> TYPE: DNA
<213> ORGANISM: Artificial Sequence
<220> FEATURE:
<223> OTHER INFORMATION: Synthetic DNA fragment inserted between two
      BbsI restriction sites of plasmid pZmU3-gRNA

<400> SEQUENCE: 7
agcagtcggc ggcgtggtcg agct                                              24

<210> SEQ ID NO 8
<211> LENGTH: 24
<212> TYPE: DNA
<213> ORGANISM: Artificial Sequence
<220> FEATURE:
<223> OTHER INFORMATION: Synthetic DNA fragment inserted in forward
      direction between two BsaI restriction sites of plasmid pBUE411

<400> SEQUENCE: 8
ggcggtcggc ggcgtggtcg agct                                              24

<210> SEQ ID NO 9
<211> LENGTH: 20
<212> TYPE: DNA
<213> ORGANISM: Arabidopsis thaliana

<400> SEQUENCE: 9
acgatatccg ccgatttcac                                                   20

<210> SEQ ID NO 10
<211> LENGTH: 24
<212> TYPE: DNA
<213> ORGANISM: Artificial Sequence
<220> FEATURE:
<223> OTHER INFORMATION: Synthetic DNA fragment inserted in a forward
      direction between two BsaI restriction sites of plasmid pHSN401

<400> SEQUENCE: 10
attggtgaaa tcggcggata tcgt                                              24

<210> SEQ ID NO 11
<211> LENGTH: 23
<212> TYPE: DNA
<213> ORGANISM: Zea mays

<400> SEQUENCE: 11
ccgagctcga ccacgccgcc gac                                               23

<210> SEQ ID NO 12
<211> LENGTH: 24
<212> TYPE: DNA
<213> ORGANISM: Artificial sequence
<220> FEATURE:
<223> OTHER INFORMATION: Synthetic fragment for insertion between the
      two BbsI restriction sites in pZmU3-gRNA plasmid

<400> SEQUENCE: 12
aaacagctcg accacgccgc cgac                                              24

<210> SEQ ID NO 13
<211> LENGTH: 21
<212> TYPE: DNA
<213> ORGANISM: Artificial sequence
<220> FEATURE:
<223> OTHER INFORMATION: Synthetic primer used for PCR amplification of
      Zea mays gene ZmIPK (Genbank No. AY172635)

<400> SEQUENCE: 13
```
tcgcagcccc tggcagagca a                                               21

<210> SEQ ID NO 14
<211> LENGTH: 26
<212> TYPE: DNA
<213> ORGANISM: Artificial Sequence
<220> FEATURE:
<223> OTHER INFORMATION: Synthetic primer used for PCR amplification of
      Zea mays gene ZmIPK (Genbank No. AY172635)

<400> SEQUENCE: 14
gagacctggg agaaggagac ggatcc                                          26

<210> SEQ ID NO 15
<211> LENGTH: 18
<212> TYPE: PRT
<213> ORGANISM: Artificial Sequence
<220> FEATURE:
<223> OTHER INFORMATION: Synthetic cell-penetrating peptide

<400> SEQUENCE: 15

Arg Lys Lys Arg Arg Gln Arg Arg Arg Lys Lys Arg Arg Gln Arg
1               5                   10                  15

Arg Arg

<210> SEQ ID NO 16
<211> LENGTH: 22
<212> TYPE: DNA
<213> ORGANISM: Artificial Sequence
<220> FEATURE:
<223> OTHER INFORMATION: Synthetic primer for amplification of pZmU3-
      gRNA-C1 plasmid

<400> SEQUENCE: 16
ctgccaagat caacagcaac ca                                              22

<210> SEQ ID NO 17
<211> LENGTH: 22
<212> TYPE: DNA
<213> ORGANISM: Artificial sequence
<220> FEATURE:
<223> OTHER INFORMATION: Synthetic primer for aplification of Cas9 in
      pJIT163-Ubi-Cas9

<400> SEQUENCE: 17
cttcccaagc attccctcct gt                                              22

<210> SEQ ID NO 18
<211> LENGTH: 22
<212> TYPE: DNA
<213> ORGANISM: Artificial sequence
<220> FEATURE:
<223> OTHER INFORMATION: Synthetic primer for amplification of Cas9 in
      pJIT163-Ubi-Cas9

<400> SEQUENCE: 18
cttatgccgt cccatgacct tc                                              22

<210> SEQ ID NO 19
<211> LENGTH: 25
<212> TYPE: DNA
<213> ORGANISM: Artificial sequence
<220> FEATURE:
<223> OTHER INFORMATION: Synthetic primer for amplification of gRNA
      sequence of pBUE411-C1 plasmid

<400> SEQUENCE: 19
gacaggcgtc ttctactggt gctac    25

<210> SEQ ID NO 20
<211> LENGTH: 22
<212> TYPE: DNA
<213> ORGANISM: Artificial sequence
<220> FEATURE:
<223> OTHER INFORMATION: Synthetic primer for amplification of Cas9
      sequence of pHSN411-C1

<400> SEQUENCE: 20
ctccctaagc actcgctcct gt    22

<210> SEQ ID NO 21
<211> LENGTH: 22
<212> TYPE: DNA
<213> ORGANISM: Artificial sequence
<220> FEATURE:
<223> OTHER INFORMATION: Synthetic primer for amplification of
      pHSN411-C1

<400> SEQUENCE: 21
ttctgcgtgg tctgattctc cc    22

<210> SEQ ID NO 22
<211> LENGTH: 23
<212> TYPE: DNA
<213> ORGANISM: Arabidopsis thaliana

<400> SEQUENCE: 22
ccgacgatat ccgccgattt cac    23

<210> SEQ ID NO 23
<211> LENGTH: 24
<212> TYPE: DNA
<213> ORGANISM: Artificial sequence
<220> FEATURE:
<223> OTHER INFORMATION: Synthetic fragment for insertion between the
      two BsaI restriction sites in pHSN401 plasmid

<400> SEQUENCE: 23
aaacacgata tccgccgatt tcac    24

<210> SEQ ID NO 24
<211> LENGTH: 20
<212> TYPE: DNA
<213> ORGANISM: Artificial sequence
<220> FEATURE:
<223> OTHER INFORMATION: Synthetic primer for amplification of
      Arabidopsis thaliana AtPTPA gene

<400> SEQUENCE: 24
gatgctccag ccaccatatc    20

<210> SEQ ID NO 25
<211> LENGTH: 24
<212> TYPE: DNA
<213> ORGANISM: Artificial sequence
<220> FEATURE:
<223> OTHER INFORMATION: Synthetic primer for amplification of
      Arabidopsis thaliana AtPTPA gene

<400> SEQUENCE: 25
cagttcggta caccacttat atca    24

<210> SEQ ID NO 26
<211> LENGTH: 25
<212> TYPE: DNA
<213> ORGANISM: Artificial sequence
<220> FEATURE:
<223> OTHER INFORMATION: Synthetic primer for amplification of
      pHSN401-C2 plasmid

<400> SEQUENCE: 26
tgtcccagga ttagaatgat taggc                                    25

<210> SEQ ID NO 27
<211> LENGTH: 24
<212> TYPE: DNA
<213> ORGANISM: Artificial sequence
<220> FEATURE:
<223> OTHER INFORMATION: Synthetic primer for amplification of
      pHSN401-C2 plasmid

<400> SEQUENCE: 27
aaacacgata tccgccgatt tcac                                     24

<210> SEQ ID NO 28
<211> LENGTH: 55
<212> TYPE: DNA
<213> ORGANISM: Zea mays

<400> SEQUENCE: 28
ccatgctcca ggtcgtctcc gagctcgacc acgccgccga ccaggacagc acttt   55

<210> SEQ ID NO 29
<211> LENGTH: 54
<212> TYPE: DNA
<213> ORGANISM: Artificial Sequence
<220> FEATURE:
<223> OTHER INFORMATION: mutation of maize endogenous gene ZmIPK

<400> SEQUENCE: 29
ccatgctcca ggtcgtctcc gagccgacca cgccgccgac caggacagca cttt    54

<210> SEQ ID NO 30
<211> LENGTH: 56
<212> TYPE: DNA
<213> ORGANISM: Artificial Sequence
<220> FEATURE:
<223> OTHER INFORMATION: mutation of maize endogenous gene ZmIPK

<400> SEQUENCE: 30
ccatgctcca ggtcgtctcc gagcatcgac cacgccgccg accaggacag cacttt  56

<210> SEQ ID NO 31
<211> LENGTH: 47
<212> TYPE: DNA
<213> ORGANISM: Artificial Sequence
<220> FEATURE:
<223> OTHER INFORMATION: mutation of maize endogenous gene ZmIPK

<400> SEQUENCE: 31
ccatgctcca ggtcgtctcc gcacgccgcc gaccaggaca gcacttt            47

<210> SEQ ID NO 32
<211> LENGTH: 45
<212> TYPE: DNA
<213> ORGANISM: Artificial Sequence
<220> FEATURE:
<223> OTHER INFORMATION: mutation of maize endogenous gene ZmIPK
<210> SEQ ID NO 32
<211> LENGTH: 45
<212> TYPE: DNA
<213> ORGANISM: Artificial Sequence
<220> FEATURE:
<223> OTHER INFORMATION: mutation of maize endogenous gene ZmIPK

<400> SEQUENCE: 32
ccatgctcca ggtcgtctcc gagccgccga ccaggacagc acttt    45

<210> SEQ ID NO 33
<211> LENGTH: 50
<212> TYPE: DNA
<213> ORGANISM: Artificial Sequence
<220> FEATURE:
<223> OTHER INFORMATION: mutation of maize endogenous gene ZmIPK

<400> SEQUENCE: 33
ccatgctcca ggtcgtctcc gagccacgcc gccgaccagg acagcacttt    50

<210> SEQ ID NO 34
<211> LENGTH: 49
<212> TYPE: DNA
<213> ORGANISM: Artificial Sequence
<220> FEATURE:
<223> OTHER INFORMATION: mutation of maize endogenous gene ZmIPK

<400> SEQUENCE: 34
ccatgctcca ggtcgtctcc gaccacgccg ccgaccagga cagcactttt    49

<210> SEQ ID NO 35
<211> LENGTH: 53
<212> TYPE: DNA
<213> ORGANISM: Artificial Sequence
<220> FEATURE:
<223> OTHER INFORMATION: mutation of maize endogenous gene ZmIPK

<400> SEQUENCE: 35
ccatgctcca ggtcgtctcc gagcgaccac gccgccgacc aggacagcac ttt    53

<210> SEQ ID NO 36
<211> LENGTH: 56
<212> TYPE: DNA
<213> ORGANISM: Artificial Sequence
<220> FEATURE:
<223> OTHER INFORMATION: mutation of maize endogenous gene ZmIPK

<400> SEQUENCE: 36
ccatgctcca ggtcgtctcc gagcttcgac cacgccgccg accaggacag cacttt    56

<210> SEQ ID NO 37
<211> LENGTH: 48
<212> TYPE: DNA
<213> ORGANISM: Artificial Sequence
<220> FEATURE:
<223> OTHER INFORMATION: mutation of maize endogenous gene ZmIPK

<400> SEQUENCE: 37
ccatgctcca ggtcgtctcc gacacgccgc cgaccaggac agcacttt    48

<210> SEQ ID NO 38
<211> LENGTH: 44
<212> TYPE: DNA
<213> ORGANISM: Artificial Sequence
<220> FEATURE:
<223> OTHER INFORMATION: mutation of maize endogenous gene ZmIPK

<400> SEQUENCE: 38
ccatgctcca ggtcgtctcc gagcgccgac caggacagca cttt    44

<210> SEQ ID NO 39

```
<211> LENGTH: 46
<212> TYPE: DNA
<213> ORGANISM: Artificial Sequence
<220> FEATURE:
<223> OTHER INFORMATION: mutation of maize endogenous gene ZmIPK

<400> SEQUENCE: 39
ccatgctcca ggtcgtctcc gagcccgccg accaggacag cacttt          46

<210> SEQ ID NO 40
<211> LENGTH: 53
<212> TYPE: DNA
<213> ORGANISM: Artificial Sequence
<220> FEATURE:
<223> OTHER INFORMATION: mutation of maize endogenous gene ZmIPK

<400> SEQUENCE: 40
ccatgctcca ggtcgtctcc gagcgaccac gccgccgacc aggacagcac ttt     53

<210> SEQ ID NO 41
<211> LENGTH: 70
<212> TYPE: DNA
<213> ORGANISM: Arabidopsis thaliana

<400> SEQUENCE: 41
ctatcatttc caatctcccg tcaaacgaat ccactctccc gacgatatcc gccgatttca  60
cgaatccgct                                                        70

<210> SEQ ID NO 42
<211> LENGTH: 21
<212> TYPE: DNA
<213> ORGANISM: Artificial Sequence
<220> FEATURE:
<223> OTHER INFORMATION: mutation of Arabidopsis endogenous gene AtPTPA

<400> SEQUENCE: 42
ctatcatttc acgaatccgc t                                           21

<210> SEQ ID NO 43
<211> LENGTH: 71
<212> TYPE: DNA
<213> ORGANISM: Artificial Sequence
<220> FEATURE:
<223> OTHER INFORMATION: mutation of Arabidopsis endogenous gene AtPTPA

<400> SEQUENCE: 43
ctatcatttc caatctcccg tcaaacgaat ccactctccc gacgtatatc cgccgatttc  60
acgaatccgc t                                                      71

<210> SEQ ID NO 44
<211> LENGTH: 69
<212> TYPE: DNA
<213> ORGANISM: Artificial Sequence
<220> FEATURE:
<223> OTHER INFORMATION: mutation of Arabidopsis endogenous gene AtPTPA

<400> SEQUENCE: 44
ctatcatttc caatctcccg tcaaacgaat ccactctccc gacatatccg ccgatttcac  60
gaatccgct                                                         69

<210> SEQ ID NO 45
<211> LENGTH: 63
<212> TYPE: DNA
<213> ORGANISM: Artificial Sequence
```

```
<220> FEATURE:
<223> OTHER INFORMATION: mutation of Arabidopsis endogenous gene AtPTPA

<400> SEQUENCE: 45
ctatcatttc caatctcccg tcaaacgaat ccactctccc gacgacgatt tcacgaatcc     60
gct                                                                  63

<210> SEQ ID NO 46
<211> LENGTH: 60
<212> TYPE: DNA
<213> ORGANISM: Artificial Sequence
<220> FEATURE:
<223> OTHER INFORMATION: mutation of Arabidopsis endogenous gene AtPTPA

<400> SEQUENCE: 46
ctatcatttc caatctcccg tcaaacgaat ccactctccc gacgatttca cgaatccgct    60

<210> SEQ ID NO 47
<211> LENGTH: 38
<212> TYPE: DNA
<213> ORGANISM: Artificial Sequence
<220> FEATURE:
<223> OTHER INFORMATION: mutation of Arabidopsis endogenous gene AtPTPA

<400> SEQUENCE: 47
ctatcatttc caatatccgc cgatttcacg aatccgct                            38
```